US005753459A

United States Patent [19]

Blanco et al.

[11] Patent Number: 5,753,459

[45] Date of Patent: May 19, 1998

[54] **NUCLEOTIDE SEQUENCES OF *T. PALLIDUM* RARE OUTER MEMBRANE PROTEIN**

[75] Inventors: David R. Blanco, Beverly Hills; James N. Miller, Northridge; Michael A. Lovett, Los Angeles; Cheryl I. Champion, Culver City, all of Calif.; Paul J. Tempst, New York, N.Y.

[73] Assignees: The Regents of the University of California, Oakland, Calif.; Sloan-Kettering Institute for Cancer Research, New York, N.Y.

[21] Appl. No.: 599,480

[22] Filed: Jan. 23, 1996

Related U.S. Application Data

[63] Continuation-in-part of Ser. No. 292,904, Aug. 17, 1994, which is a continuation-in-part of Ser. No. 255,322, Jun. 7, 1994, which is a continuation-in-part of Ser. No. 178,084, Jan. 6, 1994, abandoned.

[51] Int. Cl.[6] .......................... C12P 21/00; C07H 21/04; C07H 21/02

[52] U.S. Cl. ...................... 435/69.1; 536/23.1; 536/24.32

[58] Field of Search ................................ 536/23.1, 22.1, 536/24.32; 435/69.1; 530/350

[56] References Cited

U.S. PATENT DOCUMENTS

| | | | |
|---|---|---|---|
| 5,110,589 | 5/1992 | Joens et al. | 424/92 |
| 5,169,757 | 12/1992 | Yamazaki et al. | 435/7.92 |

FOREIGN PATENT DOCUMENTS

| | | |
|---|---|---|
| WO9518632 | 7/1995 | WIPO . |

OTHER PUBLICATIONS

Blanco, et al., *Infection and Immunity, 56*:168–175, Jan. 1988; Antigenic and Structural Characterization of *Treponema pallidum* (Nichols Strain) Endoflagella.

Blanco, et al. *Journal of Bacteriology, 176*:6088–6099, Oct. 1994; Isolation of the Outer Membranes from *Treponema pallidum* and *Treponema vincentii*.

E.H. Walker, et al., *J. of Bacteriology, 171*:5005–5011, 1989; Demonstration of Rare Protein in the Outer Membrane of *Treponema pallidum* subsp. *pallidum* by Freeze-Fracture Analysis.

S. Tomlinson, *Biochemistry, 28*:8303–8311, 1989; Transfer of Phospholipid and Protein into the Envelope of Gram-Negative Bacteria by Liposome Fusion.

J.D. Radolf, et al., *Infection and Immunity, 57*:1248–1254, 1989; Penicillin-Binding Proteins and Peptidoglycan of *Treponema pallidum* subsp. *pallidum*.

J.D. Radolf, et al., *Proc. Natl. Acad. Sci. USA, 86*:2051–2055, 1989; Outer Membrane Ultrastructure Explains the Limited Antigencity of Virulent *Treponema pallidum*.

T.M. Cunningham, et al., *J. of Bacteriology, 169*: 5298–5300, 1987; Identification of *Treponema pallidum* Penicillin-Binding Proteins.

T.M. Cunningham, et al., *J. of Bacteriology, 170*:5789–5796, 1988; Selective Release of the *Treponema pallidum* outer Membrane and Associated Polypeptides with Triton X-114.

D.R. Akins, *Infection and Immunity, 61*:1202–1210, 1993; Lipid Modification of the 17-Kilodalton Membrane Immunogen of *Treponema pallidum* Determines Macrophage Activation As Well as Amphiphilicity.

C.W. Penn, et al., *Immunology, 46*:9–16, 1982; Surface-associated Antigens of *Treponema pallidum* Concealed by an Inert Outer Layer.

E.W. Penn, et al., *J. of Gen. Micro., 131*:2349–2357, 1985; The Outer Membrane of *Treponema pallidum*: Biological Significance and Biochemical Properties.

S.J. Norris, et al., *Microbiological Reviews, 57*:750–779, 1993; Polypeptides of *Treponema pallidum*: Progress Toward Understanding Their Structural, Functional, and Immunologic Roles.

Moskophidis, et al., *Abstract, 259*:468–476, 1985; Identification of Glycosylated Protein Antigens of of *Treponema Pallidum* and *Treponema-phagedeus*. Zentralbl. Bakteriol. Mikrobiol. Hyg. Ser. A.

Norris and Sell (1984) J. Immunol. 133:2686–92.

Alderete and Baseman (1980) Infection and Immunity 30:814–23.

Hindersson et al. (1992) Res. Microbiol. 143:629–39.

Radolf et al. (1985) Infection and Immunity 63:4244–52.

Peterson et al. (1986) 164:1160–70.

Radolf (1995) Molecular Microbiology 16:1067–73.

Cunningham, Thomas Marvin (1987) Ph.D. Thesis Dissertation entitled *Identification, Isolation and Partial Characterization of Treponema Pallidum Outer Membrane Proteins.*

Champion, Cheryl Irene (1990) Ph.D. Thesis Dissertation entitled *Molecular, Structural and Functional Analysis of Treponema Pallidum subsp. PAllidum Endoflagella.*

*Primary Examiner*—W. Gary Jones
*Assistant Examiner*—Amy Atzel
*Attorney, Agent, or Firm*—Fish & Richardson P.C.

[57] ABSTRACT

Antigenic rare outer membrane proteins of Spirochaetaceae are obtained from organisms extracted from infected tissue by a novel process of isolation utilizing a discontinuous Ficoll gradient separation, release of outer membrane in a low isotonic and low pH buffer and identification of outer membrane by use of a lipid soluble dye. Four antigenic rare outer membrane proteins of *T. pallidum* subsp. pallidum useful in diagnosis and prophylaxis of syphilis are provided. Also provided are the amino acid sequences of two rare outer membrane proteins of *T. pallidum* subsp. pallidum, called TROMP 1 and TROMP 2, and the nucleotide sequences encoding them.

11 Claims, 14 Drawing Sheets

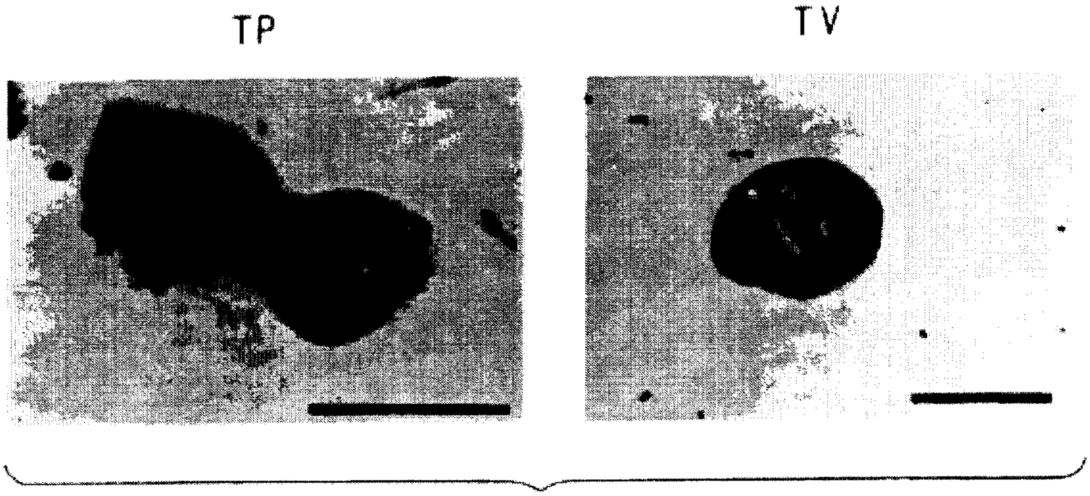
F I G. 2C
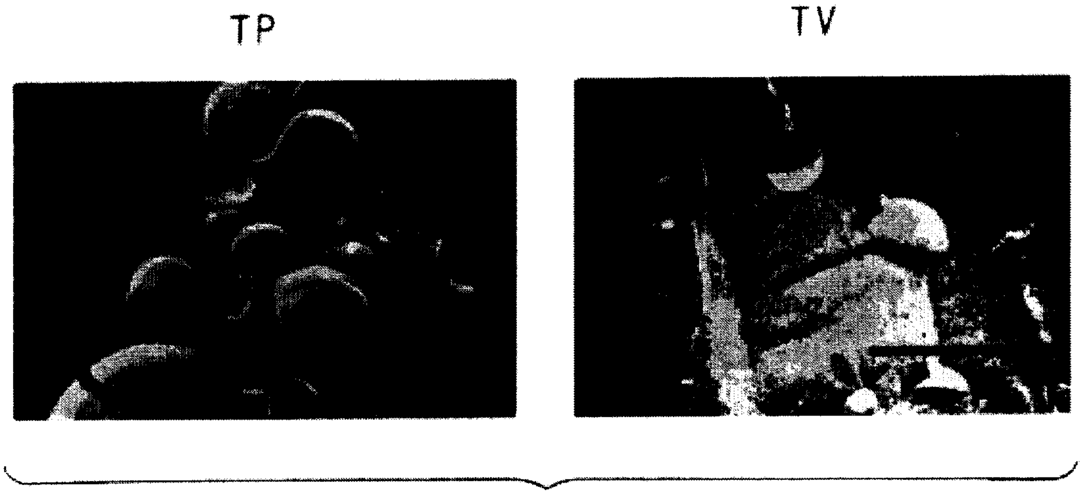
F I G. 2D

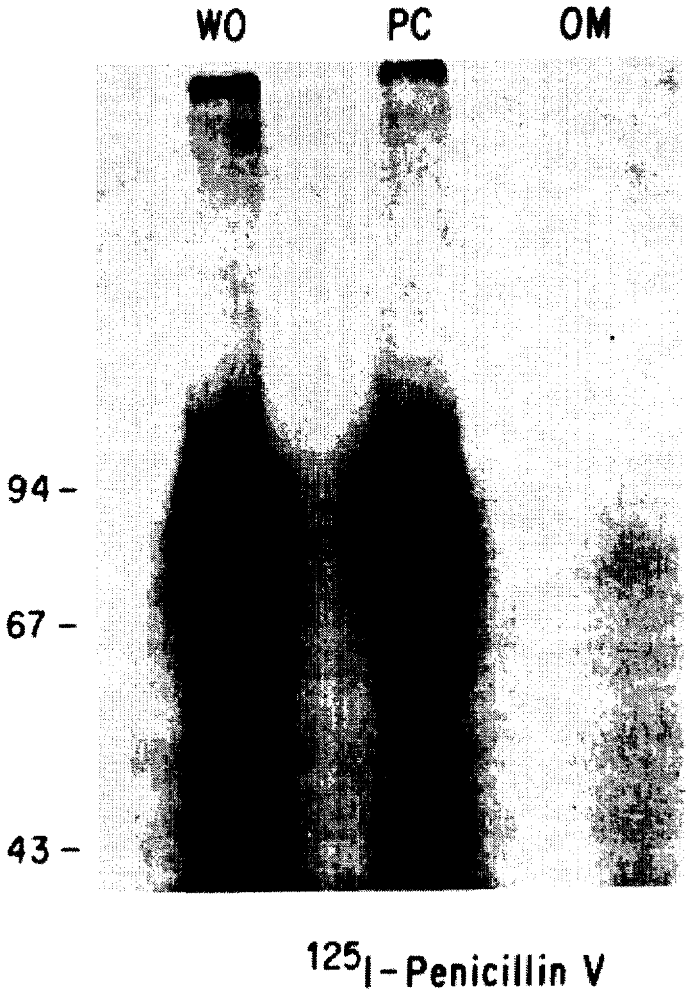
F I G. 4

```
314   /    1                                      344   /    11
ATG CAT CAA AAT TCA CCC AAG CAG TGT CAC TTG ATA CGT GAA AGA ATA TGT GCC TGC GTG
met his gln asn ser pro lys gln cys his leu ile arg glu arg ile cys ala cys val
374   /   21                                      404   /    31
CTC GCG CTT GGC ATG CTG ACC GGT TTT ACG CAC GCA TTC GGT AGC AAG GAT GCC GCA GCG
leu ala leu gly met leu thr gly phe thr his ala phe gly ser lys asp ala ala ala
434   /   41                                      464   /    51
GAC GGG AAA CCC CTG GTT GTC ACC ACC ATT GGC ATG ATA GCG GAT GCT GTC AAA AAC ATC
asp gly lys pro leu val val thr thr ile gly met ile ala asp ala val lys asn ile
494   /   61                                      524   /    71
GCT CAA GGT GAT GTG CAT CTA AAG GGG TTG ATG GGT CCT GGT GTT GAC CCG CAC CTG TAC
ala gln gly asp val his leu lys gly leu met gly pro gly val asp pro his leu tyr
554   /   81                                      584   /    91
ACG GCT ACT GCG GGG GAT GTG GAA TGG CTC GGG AAT GCG GAT CTC ATC CTG TAC AAC GGG
thr ala thr ala gly asp val glu trp leu gly asn ala asp leu ile leu tyr asn gly
614   /  101                                      644   /   111
TTG CAC CTG GAA ACC AAG ATG GGC GAG GTG TTT TCC AAA CTG CGC GGG AGC CGC TTG GTA
leu his leu glu thr lys met gly glu val phe ser lys leu arg gly ser arg leu val
674   /  121                                      704   /   131
GTT GCA GTT TCT GAG ACT ATT CCG GTG TCT CAG CGT CTT TCT CTT GAG GAA GCA GAG TTC
val ala val ser glu thr ile pro val ser gln arg leu ser leu glu glu ala glu phe
734   /  141                                      764   /   151
GAT CCG CAT GTG TGG TTT GAT GTA AAG CTG TGG TCT TAT TCG GTG AAG GCA GTG TAC GAA
asp pro his val trp phe asp val lys leu trp ser tyr ser val lys ala val tyr glu
```

FIG.10A

```
794  /  161                              824  /  171
AGC TTG TGC AAG CTG TTG CCG GGA AAA ACT CGC GAA TTT ACT CAA CGT TAT CAG GCG TAC
ser leu cys lys leu leu pro gly lys thr arg glu phe thr gln arg tyr gln ala tyr
854  /  181                              884  /  191
CAG CAG CAG TTG GAT AAG CTT GAC GCG TAC GTT CGG CGC AAG GCG CAG TCG CTG CCT GCT
gln gln gln leu asp lys leu asp ala tyr val arg arg lys ala gln ser leu pro ala
914  /  201                              944  /  211
GAA AGG CGT GTG TTG GTG ACC GCT CAT GAT GCG TTC GGC TAT TTT AGC CGT GCG TAT GGT
glu arg arg val leu val thr ala his asp ala phe gly tyr phe ser arg ala tyr gly
974  /  221                              1004 /  231
TTT GAG GTG AAG GGG TTG CAA GGG GTG AGC ACC GCT TCG GAA GCC AGT GCG CAT GAT ATG
phe glu val lys gly leu gln gly val ser thr ala ser glu ala ser ala his asp met
1034 /  241                              1064 /  251
CAG GAA CTG GCA GCG TTT ATT GCG CAG CGT AAA CTC CCT GCT ATC TTT ATT GAG AGT TCT
gln glu leu ala ala phe ile ala gln arg lys leu pro ala ile phe ile glu ser ser
1094 /  261                              1124 /  271
ATT CCG CAC AAA AAC GTT GAA GCG TTA AGG GAT GCG GTG CAG GCA AGA GGG CAC GTA GTG
ile pro his lys asn val glu ala leu arg asp ala val gln ala arg gly his val val
1154 /  281                              1184 /  291
CAG ATT GGA GGC GAG TTG TTT TCT GAT GCG ATG GGG GAT GCG GGT ACG AGC GAG GGT ACC
gln ile gly gly glu leu phe ser asp ala met gly asp ala gly thr ser glu gly thr
1214 /  301                              1244 /  311
TAC GTA GGG ATG GTA ACA CAC AAT ATC GAT ACG ATC GTT GCT GCG TTG GCT CGC TAG
tyr val gly met val thr his asn ile asp thr ile val ala ala leu ala arg AMB
```

FIG.10B

-36
CCTCGAGCGTTAGGGCTGGTGAAGAAAGGTTTGCGA 1 60
ATG AAA CAG GGC TGT TTT ATG GTG GCG GGC TTT GCG CTG ACG TGC GCG TTT TTG GTG TCC
M K Q G C F M V A G F A L T C A F L V S 61 120
CCC CTT GCG GCG CAA AGG TCG AAG GTC AAT TAC CAG GCA TAC TTC ATA GAT GAC TTT GAC
P L A A Q R S K V N Y Q A Y F I D D F D 121 180
GGT GCC TCC GAG GAT CAG GGT CTC GCC TGG CGT GCT GCG GGG AGC AAG TTC ATC ACA AAG
G A S E D Q G L A W R A A G S K F I T K 181 240
GGC TTC CCT ATC CTC AAG TAT TTC GAG GGC ATG CCA CAG GCG GTG CGC ATG GCG GGC TCG
G F P I L K Y F E G M P Q A V R M A G S 241 300
TGG CAA GGG AAG GAC AAG GAA GCC CGG TTC ATC GGA GTA GAG TGC AAG TTC AAT CGA CAG
W Q G K D K E A R F I G V E C K F N R Q 301 360
GGG AAT AAC TGG CTG GAC CTA ATT CCG ACT AAG GGT GGT AGC GAT TAC GAG ATC CCC CTG
G N N W L D L I P T K G G S D Y E I P L 361 420
CGT GGG GTG GTC AGT GGG TTC GAC GTG TGG GTG TGG GGT GCA GGT TAT CAG TAC TCG CTC
R G V V S G F D V W V W G A G Y Q Y S L 421 480
GAG GCT TTG GTT AGG GAC TGC ACG GGA CGA GTC CAC ACC CTC CTA ATA GGC AAC CTC GAC
E A L V R D C T G R V H T L L I G N L D 481 540
TTC CAA GGG TGG AAG AAC CTT AGT GTT TCG GTT CCC ACA CAC ATC CCA CAG ACG TCG CGC
F Q G W K N L S V S V P T H I P Q T S R 541 600
TAT TTG GGG AGC GCG CAA CAC CTG AGT TTT GTC GGT TTC AGG ATC CGT ACT AGC CCA TCA
Y L G S A Q H L S F V G F R I R T S P S 601 660
GAG CGG GTG GAT GAT TTC TAC GTG TTC TTT GAC CAG TTC AAG GCG CTT GCT AAC ATG CAT
E R V D D F Y V F F D Q F K A L A N M H 661 720
ATC GAC TTT TAC GAT GGA CAC GAG TTG AGA AAT GCT CAG TTC AAG GAG GAA GGA GAG AGC
I D F Y D G H E L R N A Q F K E E G E S 721 780
GGC AAA TGA
G K

FIG.11

NUCLEOTIDE SEQUENCES OF *T. PALLIDUM* RARE OUTER MEMBRANE PROTEIN

This application is a Continuation-in-Part Application of U.S. Ser. No. 08/292,904, filed Aug. 17, 1994, which is a Continuation-in-Part Application of U.S. Ser. No. 08/255,322, filed Jun. 7, 1994, which is a Continuation-in-Part Application of U.S. Ser. No. 08/178,084 filed Jan. 6, 1994 now abandoned.

This work was supported by U.S. Government NIH grant Nos. AI 21352 and AI 29733.

BACKGROUND OF THE INVENTION

1. Field of the Invention

This invention relates to methods for isolation of rare proteins from bacterial samples. More particularly, this invention relates to a method for isolating rare outer membrane proteins from the family Spirochaetaceae, such as genus Treponema and to the use of such proteins in diagnosis and prophylaxis of related diseases.

2. Description of Related Art

The genus Treponema (order Spirochaetales, family Spirochaetaceae), a type of gram-negative bacteria, contains four human pathogens as well as at least six nonpathogens. The pathogens are characterized by an extreme sensitivity to environmental conditions that renders them impossible to culture in vitro. Due to DNA homology the agents that cause syphilis, yaws and endemic syphilis have been combined into one species and three subspecies: *T. pallidum* subsp. pallidum (syphilis); *T. pallidum* subsp. pertenue (yaws); and *T. pallidum* subsp. endemicum (endemic syphilis). *T. carateum*, which is the causative agent of pinta, remains a separate species. Syphilis is found worldwide, yaws is endemic in the tropics, pinta is prevalent in tropical areas of Central and South America, and endemic syphilis is restricted to desert regions. These treponemal infections are very complex, each exhibiting distinct stages of symptomatic manifestations followed by asymptomatic periods. Without antibiotic therapy, these diseases are chronic and may last for 30 to 40 years.

To date, the four pathogens have been considered antigenically identical. An individual subspecies-specific antigen has not been identified and serological reactions demonstrate immunological relatedness. Both Wassermann and anti-*T. pallidum* subsp. pallidum antibodies develop in response to each treponemal disease, and known protective immunogens are also related, as shown by cross-resistance (T. B. Turner, et al., *Biology of the Treponematoses. W.H.O Monogr. Ser.* 35:1–277, 1957). Therefore, the geographical location together with the clinical manifestations of the patient have been considered the key to diagnosis (*Manual of Clinical Microbiology,* 5th Ed., A. Balows, et al., Eds., p 567, 1991).

Freeze-fracture electron microscopy of outer membranes from pathogenic spirochetes has revealed that their integral transmembrane outer membrane protein density is one to two orders of magnitude less than that of typical gram negative bacterial pathogens. It has been proposed that this low outer membrane composition, and thus low surface exposure of antigenic target molecules, allows these organisms to effectively evade the host immune response, contributing to the chronic nature of infection exhibited by all spirochetal pathogens.

As is well known, the outer membranes of spirochetes, including that of *Treponema pallidum* subsp. pallidum, the agent of syphilis, are fragile structures as compared to those of typical gram negative bacteria. Consequently, separation of the outer membrane from the inner membrane has proven extremely difficult. Certain other medically relevant spirochetal bacteria with outer membrane structure and, hence, protein structure, similar to those of *T. pallidum* include *Borrelia burgdorferi* (Lyme Disease), Borrelial species (relapsing fever), and Leptospiral species (leptospirosis).

The outer membrane of *T. pallidum* has been found to be antigenically inert and resistant to specific treponemidical antibody (Radolf, et al., *Infect. Immun.,* 52:579, 1986; Hovind-Hougen, et al., *Acta Pathol. Microbiol. Scand . . . ,* 87:263, 1979; Nelson, et al., *J. Exp. Med.,* 89:369, 1949). Yet freeze-fracture electron microscopy has shown that certain rare outer membrane protein (tromp) molecules of *T. pallidum* have surface exposed antigenic sites that bind antibody present in the serum of challenge immune animals (Blanco, et al., *J. Immunol.,* 144:1914–1921, 1990). Taken together, the spirochetal bacterial pathogens imperil the health of a considerable portion of the human population, yet development of effective and specific vaccines and isolation of antigens capable of generating protective immune response has been hampered by a considerable number of problems associated with this organism: the impossibility of culturing the *T. pallidum* in vitro, the limited numbers of organisms that can be obtained from infected animals, the contamination of treponemes by host tissue components, the fragility of the treponemal outer membrane, and the difficulty of isolating and identifying the outer membrane proteins of pathogenic spirochetes.

Previous studies attempting to identify transmembrane outer membrane proteins of pathogenic spirochetes have utilized various detergent solubilization approaches. Spirochetal outer membranes bleb from the underlying protoplasmic cylinder under relatively mild conditions, including dilute detergents and hypotonic environments. However, such approaches have identified only abundant subsurface located proteins, including various lipoproteins which by definition are not transmembrane molecules and do not form particles viewed by freeze-fracture analysis.

Therefore, the need exists for new and better vaccines based upon the identification of virulence related outer membrane molecules to be used in diagnosis and for prophylaxis of diseases related to the pathogenic spirochetal bacteria, especially the genus *T. pallidum.*

SUMMARY OF THE INVENTION

A novel method is provided for isolating outer membrane of pathogenic Spirochaetacae family without use of detergents. The pathogen is purified from contaminating host components using a density gradient centrifugation medium that is stable at pH from about 3.2 to about 3.0, preferably a Ficoll step gradient. The purified pathogen is treated with a lipid soluble chromophore that intercalates into outer membrane to provide a visual marker of membrane matter. Outer membrane is released from protoplasmic cylinders using a hypotonic, low pH buffer, preferably citrate, followed by density gradient centrifugation, which yields, for example, the chromophore labeled bands at 7% and 35% sucrose (wt/vol) for *T. pallidum* and *T. vincentii*, respectively. Freeze-fracture electron microscopy of membrane vesicles from the spirochete reveals an extremely low density of protein particles. For instance, the particle density of *T. pallidum* is approximately six times less than that of *T. vincentii.* Comparative immunoblot analysis of the *T. vincentii* membrane material to that of whole organisms showed a lipopolysaccharide (LPS) ladder consistent with 20% recovery of the outer membrane. Immunoblots of *T. vincentii* outer membrane also showed two antigenic proteins at 55- and 65-kDa.

$^{125}$I-penicillin, which binds only to inner membrane and not to outer membrane, was used to detect the presence of any inner membrane in the outer membrane preparation isolated according to the method of the invention. No penicillin binding proteins in the *T. pallidum* membrane material were detected, indicating the absence of inner membrane contamination.

Immunoblot analysis of *T. pallidum* outer membrane using antibodies specific for periplasmic associated proteins showed no detection of known 19-kDa "4D" protein or the 47-kDa lipoprotein, and only trace amounts of endoflagellar protein. Rare outer membrane proteins associated with the *T. pallidum* were detected by one and two dimensional reducing SDS-PAGE separation and immunoblot analysis, using gold staining and serum from infected and challenge immune animals. As compared to whole organism preparations, four of the isolated proteins were obtained in significantly enriched amounts from the outer membrane preparation.

Methods are provided for the use of outer membrane proteins of pathogenic Spirochaetacae family for detection and amelioration of associated disease states.

The isolation of the *T. pallidum* outer membrane and identification of its protein constituents has been complicated by the fragility of this structure, the limited number of treponemes that can be acquired by rabbit infection, and the significant amount of host contaminating protein following extraction of organisms from infected animals. Moreover, freeze-fracture electron microscopy has revealed that the outer membrane of *T. pallidum* contains two orders of magnitude less integral membrane protein than typical gram negative bacteria (Radolf, et al., *Proc. Natl. Acad. Sci. USA*, 86:2051–2055, 1989; Walker, et al., *J. Bacteriol.*, 171:5005–5011, 1989). Because of the paucity of *T. pallidum* rare outer membrane protein (TROMP), it is likely that previous studies using detergent extraction of *T. pallidum* to identify transmembrane outer membrane proteins have mistakenly identified as outer membrane proteins abundant subsurface molecules, including lipoproteins anchored in the inner membrane that are released by such treatments (Chamberlain, et al., *Infect. Immun.*, 57:2872–2877, 1989; Penn, et al., *Immunology*, 46:9–16, 1982; Penn, et al., *J. Gen. Microbiol.*, 131:2349–2357, 1985).

It has previously been shown that while 0.1% Triton X-114 can selectively solubilize the *T. pallidum* outer membrane, some subsurface molecules, including the 47-kDa lipoprotein, are also released (Radolf, et al., *Infect. Immun.*, 56:490–498, 1988). Concentrations of Triton X-114 of up to 2% have been shown to release additional *T. pallidum* lipoproteins (Cunningham, et al., *J. Bacteriol.*, 170:5789–5796, 1988; Radolf, et al., supra, 1988).

The present invention provides a method for isolating the outer membranes from treponemes and other spirochetes with rare outer membrane proteins in the absence of detergents. In the examples herein this procedure was applied to *T. vincentii*, which, because of the LPS content of its outer membrane, was used as a marker for outer membrane recovery. Preliminary studies showed that while a hypotonic osmotic environment caused significant blebbing of the treponemal outer membrane, only a small amount of outer membrane was released. Endoflagellar filaments may physically interact with the outer membrane in the process of motility (Berg, *J. Theor. Biol.*, 56:269–273, 1976; Goldstein, et al., *Cell Motility and the Cytoskeleton*, 9:101–110, 1988). These structures may limit the release of outer membrane under hypotonic conditions. Therefore, in the present invention a low pH hypotonic buffer is used to dissociate endoflagellar filaments (Blanco, et al., *Infect. Immun.*, 56:168–175, 1988). As a result, the outer membrane is completely released as viewed by electron microscopy. The low pH treatment, however, is incompatible with purification of *T. pallidum* by the conventional Percoll procedure due to the adverse effects of low pH on residual Percoll, which solubilizes in low pH conditions. Therefore, in the practice of this invention, *T. pallidum* is purified using a continuous or discontinuous density gradient separation in a medium that is stable in the pH range from 3.2 to 3.0, removes contaminating host components, and is also compatible with the subsequent low pH incubation.

A second key step in the practice of this invention is treatment of treponemes with a chromophore, preferably one that intercalates into biological and liposomal membranes. The preferred chromophore is octyl-decyl rhodamine, but one skilled in the art will appreciate that any chromophore of a size suited to intercalate into liposomal membranes can be used so long as it is naturally lipophilic or can be substituted with lipid-solubilizing moieties containing between 8 and 10 carbon atoms. In addition, the lipid-soluble chromophore should be selected so as not to significantly alter the membrane particle density. Use of the chromophore provides a visual marker to follow the disposition of released outer membrane. To determine whether the chosen lipid-soluble chromophore alters membrane particle density, a pathogenic spirochete having an order of magnitude greater amount of outer membrane protein than the one being isolated can be used. For instance, using *Borrelia burgdorferi*, a pathogenic spirochete which has an order of magnitude greater amount of outer membrane protein than *T. pallidum* (Walker, et al., supra, 1991), it was found that octyl-decyl rhodamine did not change its outer membrane particle density (data not shown), suggesting that the outer membrane proteins of *T. pallidum* and *T. vincentii* were also not affected by this reagent.

The finding herein that *T. pallidum* outer membrane banded in a sucrose gradient at a very low density (7%) is consistent with membrane that contains a small amount of protein (Tomlinson, et al., *Biochem.*, 28:8303–8311, 1989). This finding was further confirmed by freeze-fracture electron microscopy of purified *T. pallidum* membrane vesicles, which showed fracture faces that contained extremely rare intramembranous particles. This result is similar to the low particle density observed by others for the native outer membrane of *T. pallidum* (Radolf, et al. supra; Walker, et al., supra). By comparison, the *T. vincentii* outer membrane banded in a sucrose gradient at a higher density (35%) as is consistent with the greater amount of intramembranous particles observed in its membrane and/or is consistent with a membrane that contains lipopolysaccharide (LPS).

The selective isolation of the *T. pallidum* outer membrane from the protoplasmic cylinder was determined by the use of penicillin binding proteins (PBPs) as a marker to visualize inner membrane associated proteins. Previously studies have shown that *T. pallidum* PBPs remain with the protoplasmic cylinders following solubilization of the outer membrane in the detergents Triton X-114 or Triton X-100 (Cunningham, et al., *J. Bacteriol.*, 169:5298–5300, 1987; Radolf, et al., *Infect. Immun.*, 57:1248–1254, 1989). No PBPs were detected with purified outer membrane prepared according to the method of this invention, indicating that the procedure selectively removes only the outer membrane, free from contamination by inner membrane.

Of particular significance is the complete absence of the *T. pallidum* outer membrane preparation of the 4D protein and the 47-kDa major lipoprotein, and the finding of only trace amounts of endoflagellar protein, indicating little to no contamination by these periplasmic components. The 47-kDa lipoprotein, one of the most abundant *T. pallidum* molecules, was not detected in the outer membrane preparation, thus confirming that inner membrane anchored lipoproteins were not released by this procedure.

Coomassie stained SDS-PAGE and immunoblot analysis of $1\times10^9$ *T. vincentii* equivalents of outer membrane revealed two major antigenic protein species of 65- and 55-kDa. In contrast, Coomassie stained SDS-PAGE of a 5-fold greater amount of *T. pallidum* outer membrane showed no detectable protein. These findings are consistent with the observations of freeze-fracture electron microscopy indicating that the outer membrane particle density of *T. pallidum* is six times less than that of *T. vincentii*. From the outer membrane particle density of *T. pallidum*, which has been determined to be 170 particles/um$^2$ and the surface area of *T. pallidum*, which is approximately 4 um$^2$, it is calculated that $5\times10^9$ *T. pallidum* should contain only 250 nano grams of outer membrane protein based upon a single species of 50K molecular weight. Therefore, the amount of a single species of TROMP isolated using the method of this invention is several hundred times less than was previously erroneously identified by prior art methods (Norris, et al., *Microbiol.,* 57:750–779, 1993).

Enhanced chemiluminescence (ECL) immunoblotting has the sensitivity of detecting pico grams of antigen (ECL Western Blotting protocols, Buckinghamshire, England, 1993). Therefore, this technique is preferably employed in the method of this invention for detecting outer membrane associated protein. Most preferably, using ECL, immunoblots of outer membrane samples are prepared in urea and electrophoresed in one dimension or following two dimensional (2D) electrophoresis, and probed with sera from rabbits with immunity to the pathogenic treponeme of interest. Using this technique upon *T. pallidum* showed two major antigenic protein bands at 17- and 45-kDa. The 17-kDa protein had a pI of greater than 7.0, showed higher oligomeric forms, and selectively partitioned into the hydrophobic phase following Triton X-114 detergent extraction (data not shown).

These findings are consistent with the properties of the native and recombinant 17-kDa lipoprotein of *T. pallidum* (Atkins, et al., *Infect. Immun.,* 61:1202–1210, 1993). It was also shown using specific monoclonal antibodies that the 45-kDa protein was the previously characterized TmpA lipoprotein (Schouls, et al., *Microb. Pathog.,* 7:175–188, 1989; Hansen, et al., *J. Bacteriol.,* 162:1227–1237, 1985). While the vast majority of these two proteins remain associated with the protoplasmic cylinder following outer membrane removal (data not shown), some of the 17- and 45-kDa lipoproteins are specifically associated with outer membrane.

In addition to the strongly antigenic 17- and 45-kDa lipoproteins of *T. pallidum* isolated, gold-stained 2D blots of $3\times10^{10}$ treponemal equivalents revealed four additional *T. pallidum* proteins, including one each at 26 and 65 kDa, and two at 31-kDa. All of these proteins have been found to contain antigenic sites reactive with sera from immune rabbits. Comparison of the pI's of these found proteins to those on 2D blots of $5\times10^8$ whole organisms have shown that the 31-kDa (acidic pI) and 26-kDa proteins correspond to prominent *T. pallidum* protein spots on immunoblots and may be additional outer membrane associated lipoproteins not heretofore identified. In contrast, the 31-kDa protein (basic form) corresponds to a minor and faintly detectable protein spot on 2D blots of whole organisms, while the 65-kDa protein does not correspond to any previously identified *T. pallidum* protein. In view of their significant enrichment following outer membrane isolation, the 31-kDa (basic pI) and 65-kDa proteins are identified as rare outer membrane proteins.

The outer membrane proteins of typical gram negative bacteria include an export signal cleaved by leader peptidase I, and amphiphathic beta pleated sheet structure throughout the secondary sequence that generates membrane spanning regions (Vogel, et al., J. *Mol. Biol .,* 190:191–199, 1986; Weiss, et al., *Science,* 254:1627–1630, 1991; Von Heijne, *J. Mol. Biol.,* 184:99–105, 1985). Recently, the gene encoding a surface exposed 31-kDa protein of *Leptospira alstoni*, designated Omp-L1 (outer membrane protein of Leptospira), has been cloned, sequenced, and expressed (Haake, et al., *J. Bacteriol.,* 175:42254234, 1993). The deduced amino acid sequence of this protein shows an export and amphiphatic beta pleated sheet topology resulting in 10 membrane spanning domains (Haake, et al., supra). The structural similarity between this putative outer membrane protein of Leptospira and those of typical gram negative bacteria suggests that other spirochetal outer membrane proteins may be structurally similar to those of typical gram negative bacteria. The Leptospira outer membrane has been isolated using the method of this invention. The membrane material purified was found to selectively contain lipopolysaccharide like substance (LLS), which is unique to the Leptospira outer membrane (Zeigler, et al., *Can. J. Microbiol.,* 21:1102–1112, 1975), and several proteins including OMP-L1. These findings provide additional evidence that the membrane material and associated protein isolated by the method of this invention from *T. pallidum* is outer membrane in origin.

The binding of antibody in immune serum to virulent *T. pallidum* results in aggregation of TROMP particle as viewed by freeze fracture electron microscopy (Blanco, et al., supra, 1990). These findings have recently been confirmed and extended using serum obtained from animals with varying degrees of challenge immunity. Particle aggregation directly correlates with the development of challenge immunity, suggesting that TROMP are key targets for a protective host immune response.

In addition, due to isolation and purification of the *T. pallidum* outer membrane, the amino acid sequence of the protein has been obtained and of DNA encoding it and for cloning of TROMP molecules. The recombinant expression of these rare outer membrane proteins can be used for experimental biology studies to address directly the molecular basis for *T. pallidum* pathogenesis, for diagnostic tests to detect syphilis and for development of host immunity during syphilis.

BRIEF DESCRIPTION OF THE DRAWINGS

FIG. 1A shows a Coomassie stained SDS-PAGE gel.

FIG. 1B shows immunoblots probed with anti-rabbit serum proteins.

FIGS. 2A–2D show electron micrographs of outer membrane material isolated from *T. pallidum* (Tp) and *T. vincentii* (Tv).

FIG. 2A shows whole mount electron micrographs of Tp purified on Ficoll and labeled with rhodamine and Tv washed with PBS and labeled with rhodamine.

FIG. 2B shows a whole mount electron micrographs of Tp and Tv organisms treated with acidic citrate buffer, showing release of outer membrane.

FIG. 2C shows whole mount electron micrographs of Tp and Tv outer membrane vesicles purified on sucrose gradient.

FIG. 2D shows freeze fracture electron micrographs of purified Tp and Tv outer membrane vesicles. Bar indicates 0.5 μm.

FIG. 4 an SDS-PAGE autoradiograph showing penicillin binding proteins from $1\times10^8$ whole organisms (WO) and protoplasmic cylinders (PC) of *T. pallidum* and from $5\times10^9$ equivalents of outer membrane (OM). The molecular weights ($\times10^3$) of marker standards are indicated.

FIG. 10 shows the nucleotide sequence for an open reading frame identified in the 872 bp HindIII fragment in the DNA of the 31 kDa TROMP protein (pI 6.7) (SEQ ID NO:1). The nucleotide sequence encodes a precursor TROMP protein of 288 amino acids known as TROMP1 (SEQ ID NO:2).

FIG. 11 shows the nucleotide sequence of the *T. Pallidum* TROMP2 gene (SEQ ID NO:3). The deduced amino acid sequence is shown below the nucleotide sequence. The TROMP2 gene encodes a precursor TROMP protein of 242 amino acids known as TROMP2 (SEQ ID NO:4), including a putative signal peptide of 24 amino acids with a type I signal peptidase cleavage site of Leu-Ala-Ala indicated by the vertical arrow.

DETAILED DESCRIPTION OF THE INVENTION

Figure 1A:
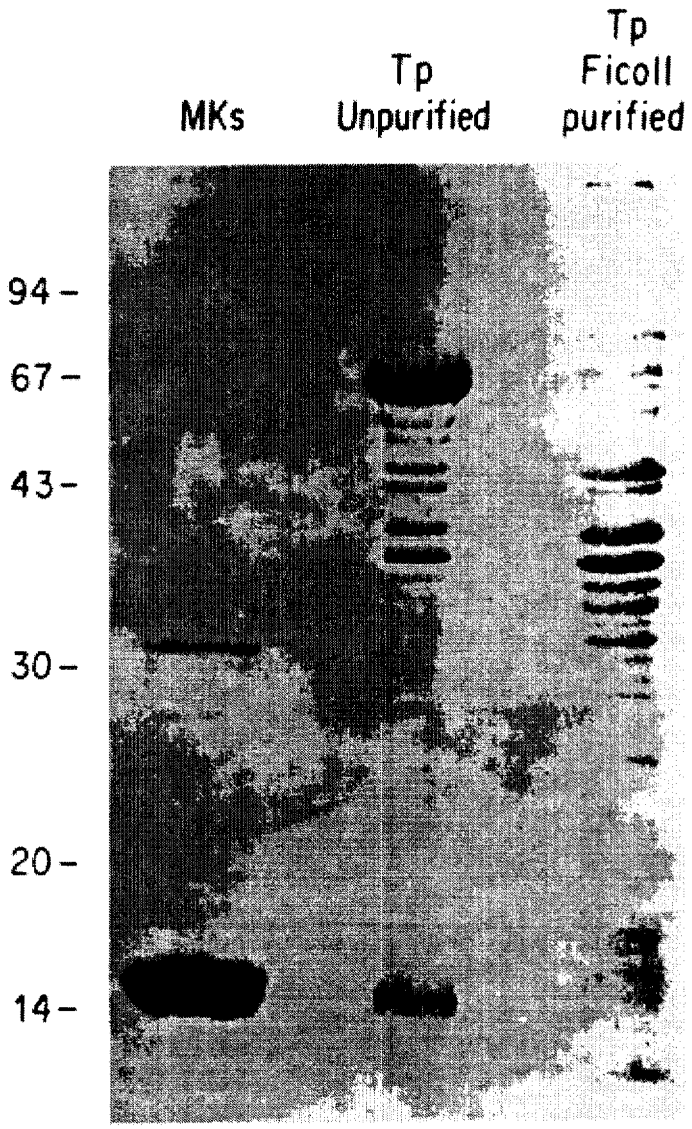
FIGS. 1A and 1B are an SDS-PAGE autoradiographs showing comparative analysis of $5\times10^8$ unpurified and Ficoll purified *T. pallidum* (Tp). The molecular weights ($\times10^3$) of marker standards (MKs) are indicated.

The present invention provides isolated and purified rare outer membrane proteins and protein fragments of the pathogenic Spirochaetacae family, especially of the genus Treponema, and a method for their isolation. These immunogenic proteins are useful in a pharmaceutical composition for inducing an immune response to pathogenic Spirochaetacae from which they are derived. Hence, the rare outer membrane proteins of this invention are useful for ameliorating the effects of disease states associated with the pathogen from which they are derived. In addition, the rare outer membrane proteins, which contain antigenic epitopes for antibodies found in the blood of infected mammals, such as humans, can be used to detect individuals infected with disease states associated with the pathogens from which the proteins are derived. Alternatively, antibodies generated from immunization of an individual with the rare outer membrane proteins can be used to detect exposure to or infection by the pathogen in another individual.

The preferred outer membrane proteins of this invention are isolated from the outer membrane of the genus *Treponema pallidum* subsp. pallidum, the pathogen responsible for causing syphilis in humans, and are characterized by the following isoelectric focus points and molecular weights, as determined by reducing SDS-PAGE as shown in Table 1.

TABLE 1

| Protein | Molecular weight | pI |
|---|---|---|
| ROM 1 | 31 kDa | 6.6 |
| ROM 2 | 65 kDa | 5.9–6.0 |
| ROM 3 | 26 kDA | 6.9–7.0 |
| ROM 4 | 31 kDa | 6.5 |

A novel method for isolating outer membrane of pathogenic Spirochaetacae family is presented herein. The pathogen is purified from contaminated host components, such as tissue, blood, bodily secretions, and the like, preferably using a discontinuous Ficoll step gradient of at least four steps. It is preferred that the densities of the discontinuous step gradient be as follows: 1.045, 1.055, 1.065 and 1.085 g/ml. The purified pathogen is treated with a lipid soluble chromophore that intercalates into outer membrane, to provide a visual marker of membrane matter. The lipid-soluble chromophore is preferably a dye marker, most preferably a fluorescent dye marker substituted with one or more branched or unbranched alkyl chains, each containing from about 8 to 10 carbon atoms.

Outer membrane is released from protoplasmic cylinders without use of detergent using a hypotonic, low pH buffer followed by density gradient centrifugation to obtain the chromophore labeled band. The buffer is kept at pH from about 3.2 to about 3.0, and the buffer is preferably citrate or acetate. Preferably, the buffer has an ionic strength of 50 mM to 100 mM.

The density gradient centrifugation medium must be selected to be stable within the low pH range of the buffer. Generally, any polymeric density gradient centrifugation medium having stability at pH within the range from about 3.2 to 3.0 can be used, but preferably the medium is a polymeric saccharide medium such as FICOLL®, a synthetic polymer of sucrose, or FICOLL HYPAQUE® density gradient medium. The centrifugation medium can be either continuous or discontinuous, but preferably in the practice of this invention the density range is from about 1.045 to about 1.085 g/ml. Although any workable means can be used, the band containing the chromophore labeled band is preferably separated from the sucrose gradient medium by needle aspiration.

Antibodies provided in the present invention are immunoreactive with at least one Spirochaetales ROM protein of the pathogen of interest. Antibody which consists essentially of pooled monoclonal antibodies with different epitopic specificities, as well as distinct monoclonal antibody preparations are provided. Monoclonal antibodies are made from antigen-containing fragments of the protein by methods well known in the art (Kohler, et al., *Nature*, 256:495, 1975; *Current Protocols in Molecular Biology*, Ausubel, et al., ed., 1989). The term antibody, or immunoglobulin, as used in this invention includes intact molecules as well as fragments thereof, such as Fab and $F(ab')_2$, that are capable of binding an epitopic determinant on a Spirochaetales ROM, such as the ROMs of *T. pallidum* shown in Table 1.

Minor modifications of primary amino acid sequence may result in proteins that have substantially equivalent function compared to the ROM proteins described herein. Such modifications may be deliberate, as by site-directed mutagenesis, or may be spontaneous. All proteins produced by these modifications are included herein as long as the antigenic function of the modified ROM is substantially intact.

Modifications of the ROM protein primary amino acid sequence contemplated by the claims herein also include conservative variations. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The invention extends to any host modified according to the methods described, or modified by any other methods, commonly known to those of ordinary skill in the art, such as, for example, by transfer of genetic material using a lysogenic phage, and which result in a prokaryote expressing the Spirochaetales gene for protein. Prokaryotes transformed with the Spirochaetales gene encoding the ROM protein are particularly useful for the production of polypeptides which can be used for the immunization of an animal.

In one embodiment, the invention provides a pharmaceutical composition useful for inducing an immune response in an animal to pathogenic Spirochaetales, preferably a Treponema, most preferably *T. pallidum*. The composition comprises an immunologically effective amount of an antigenic outer membrane protein in a pharmaceutically acceptable carrier. The term "immunogenically effective amount," as used in describing the invention, is meant to denote that amount of Spirochaetales antigen that is necessary to induce in an animal the production of an immune response to Spirochaetales. The rare outer membrane proteins of the invention are particularly useful in sensitizing the immune system of an animal such that, as one result, an immune response is produced which ameliorates the effect of Spirochaetales infection. For instance, an immune response to *T. pallidum* can be produced by administering to an animal the ROM proteins of Table 1 isolated by the method of this invention.

In another embodiment as shown in FIG. 10, the invention provides the amino acid sequence of a 288 amino acid precursor protein fragment (TROMP1) of the 31 kDa protein of this invention (SEQ ID NO:1). TROMP1 is encoded by a DNA open reading frame of 867 bp (SEQ ID NO:2). In yet another embodiment as shown in FIG. 10, the invention provides the amino acid sequence of a 242 amino acid precursor protein (TROMP2) of the 26 kDa protein of this invention (SEQ ID NO:3). TROMP2 is encoded by a DNA open reading frame of 726 bp (SEQ ID NO:4). Amino acid sequence of the tryptic peptides were used to generate mixed oligonucleotide probes, which were used to screen a *T. Pallidum* genomic library previously digested with Eco R1 restriction enzyme. The deduced amino acid sequence of TROMP 2 begins with a 24-residue hydrophobic region presumed to be a signal peptide, which is consistent with a protein exported across the cytoplasmic membrane. The mature processed protein consists of 218 residues with a calculated mass of 24,759 Da.

A *T. Pallidum* rare outer membrane protein can be administered parenterally by injection, rapid infusion, nasopharyngeal absorption, dermal absorption, or orally. Pharmaceutically acceptable carrier preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers for occlusive dressings can be used to increase skin permeability and enhance antigen absorption. Liquid dosage forms for oral administration may generally comprise a liposome solution containing the liquid dosage form. Suitable forms for suspending the liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, and sweetening, flavoring, and perfuming agents.

It is also possible for the antigenic preparations containing the Spirochaetales ROM proteins of the invention to include an adjuvant. Adjuvants are substances that can be used to nonspecifically augment a specific immune response. Normally, the adjuvant and the antigen are mixed prior to presentation to the immune system, or presented separately, but into the same site of the animal being immunized. Adjuvants can be loosely divided into several groups based on their composition. These groups include oil adjuvants (for example, Freund's Complete and Incomplete), mineral salts (for example, $AlK(SO_4)_2$, $AlNa(SO_4)_2$, $AlNH_4(SO_4)$, silica, alum, $Al(OH)_3$, $Ca_3(PO_4)_2$, kaolin, and carbon), polynucleotides (for example, poly IC and poly AU acids), and certain natural substances (for example, wax D from *Mycobacterium tuberculosis*, as well as substances found in *Corynebacterium parvum*, *Bordetella pertussis*, and members of the genus Brucella).

In another embodiment, a method of inducing an immune response to pathogenic Spirochaetales, especially Treponema such as *T. pallidum* subsp. pallidum; *T. pallidum* subsp. pertenne; *T. pallidum* subsp. endemicum; and *T. cerateum* in animal is provided. Many different techniques exist for the timing of the immunizations when a multiple immunization regimen is utilized. It is possible to use the antigenic preparation of the invention more than once to increase the levels and diversity of expression of the immune response of the immunized animal. Typically, if multiple immunizations are given, they will be spaced two to four weeks apart. Subjects in which an immune response to Spirochaetales is desirable include domestic animals and humans.

Generally, the dosage of ROM protein administered to an animal will vary depending on such factors as age, condition, sex and extent of disease, if any, and other variables which can be adjusted by one of ordinary skill in the art.

The antigenic preparations of the invention can be administered as either single or multiple dosages and can vary from about 10 ug to about 1,000 ug of the Spirochaetales ROM antigenic protein per dose, more preferably from about 50 ug to about 700 ug of ROM antigenic protein per dose, most preferably from about 50 ug to about 300 ug of ROM antigenic protein per dose.

When used for immunotherapy, the monoclonal antibodies specific for Spirochaetales ROM proteins of the invention or fragments thereof may be unlabeled or labeled with a therapeutic agent. These markers can be coupled either directly or indirectly to the monoclonal antibodies of the invention. One example of indirect coupling is by use of a spacer moiety. These spacer moieties, in turn, can be either insoluble or soluble (Diener, et al., *Science,* 231:148, 1986) and can be selected to enable drug release from the monoclonal antibody molecule at the target site. Examples of diagnostic markers that can be coupled to the monoclonal antibodies of the invention for immunotherapy of disease states associated with Spirochaetales such as *T. pallidum* are drugs, radioisotopes, lectins, and toxins. The labeled or unlabeled monoclonal antibodies of the invention can also be used in combination with therapeutic agents such as those described above.

When the monoclonal antibody of the invention is used in combination with various therapeutic agents, such as those described herein, the administration of the monoclonal antibody and the therapeutic agent usually occurs substantially contemporaneously. The term "substantially contemporaneously" means that the monoclonal antibody and the therapeutic agent are administered reasonably close together with respect to time. Usually, it is preferred to administer the therapeutic agent before the monoclonal antibody. For example, the therapeutic agent can be administered 1 to 6 days before the monoclonal antibody. The administration of the therapeutic agent can be daily, or at any other interval, depending upon such factors, for example, as the nature of the disorder, the condition of the patient and half-life of the agent.

The dosage ranges for the administration of monoclonal antibodies of the invention are those large enough to produce the desired effect in which the onset symptoms of the Spirochaetales disease are ameliorated. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician in the event of any complication. Dosage can vary from about 0.1 mg/kg to about 2000 mg/kg, preferably about 0.1 mg/kg to about 500 mg/kg, in one or more dose administrations daily, for one or several days. Generally, when the monoclonal antibodies of the invention are administered conjugated with therapeutic agents, lower dosages, comparable to those used for in vivo diagnostic imaging, can be used.

The monoclonal antibodies of the invention can be administered parenterally by injection or by gradual perfusion over time. The monoclonal antibodies of the invention can be administered intravenously, intraperitoneally, intramuscularly, subcutaneously, intracavity, or transdermally, alone or in combination with effector cells.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents and inert gases and the like.

In a further embodiment, the invention provides a method of detecting a pathogenic Spirochaetales-associated disorder in a subject comprising contacting a ROM protein of the Spirochaetales with an antibody specific therefor. The antibodies are detectably labeled, for example, with a diagnostic radioisotope, a fluorescent compound, a bioluminescent compound, a chemiluminescent compound, a metal chelator or an enzyme. Those of ordinary skill in the art will know of other suitable labels for binding to the antibody, or will be able to ascertain such, using routine experimentation.

For purposes of the invention, an antibody or nucleic acid probe specific for a Spirochaetales ROM protein may be used to detect the presence of ROM protein or fragment thereof in biological fluids or tissues. Any specimen containing a detectable amount of ROM protein antigen or polynucleotide can be used. A preferred specimen of this invention is blood, urine, cerebrospinal fluid, or tissue of skin (epidermis, dermis, and subcutaneous), spleen, liver, heart, brain, and bone origin.

Another technique that may also result in greater sensitivity consists of coupling antibodies to low molecular weight haptens. These haptens can then be specifically detected by means of a second reaction. For example, it is common to use such haptens as biotin, which reacts with avidin, or dinitrophenyl, pyridoxal, and fluorescein, which can react with specific antihapten antibodies.

Alternatively, the ROM proteins of this invention, or antibody-binding fragments thereof, can be used to detect antibodies to Spirochaetales ROM proteins in a specimen. The ROM protein of the invention is particularly suited for immunoassays in which it can be utilized in liquid phase or bound to a solid phase carrier. In addition, ROM proteins used in these assays can be detectably labeled in various ways.

Examples of immunoassays that can utilize the antibodies or ROM proteins of the invention are competitive and noncompetitive immunoassays in either a direct or indirect format. Examples of such immunoassays are the radioimmunoassay (RIA), the sandwich (immunometric assay) and the Western blot assay. Detection of antibodies which bind to the ROM proteins of the invention can be done utilizing immunoassays that run in either the forward, reverse, or simultaneous modes, including immunohistochemical assays on physiological samples. The concentration of ROM protein used will vary depending on the type of immunoassay and nature of the detectable label used. However, regardless of the type of immunoassay used, the concentration of ROM protein utilized can be readily determined by one of ordinary skill in the art using routine experimentation.

The Spirochaetales ROM protein or antibody-binding fragments thereof of the invention can be bound to many different carriers and used to detect the presence of antibody specifically reactive with the protein. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for purposes of the invention. Those skilled in the art will know of other suitable carriers for binding the ROM proteins of the invention or will be able to ascertain such, using routine experimentation.

There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds.

For purposes of the invention, the antibody which binds to ROM protein of the invention may be present in various biological fluids and tissues. Any sample containing a detectable amount of antibodies to ROM protein can be used. Normally, a sample is a liquid such as urine, saliva, cerebrospinal fluid, blood, serum and the like, or a solid or semi-solid such as tissue, feces and the like.

The monoclonal antibodies of the invention, directed toward Spirochaetales ROM proteins, are also useful for the in vivo detection of antigen. The detectably labeled monoclonal antibody is given in a dose that is diagnostically effective. The term "diagnostically effective" means that the amount of detectably labeled monoclonal antibody is administered in sufficient quantity to enable detection of Spirochaetales protein antigen for which the monoclonal antibodies are specific.

The concentration of detectably labeled monoclonal antibody administered should be sufficient such that the binding to those cells, body fluid, or tissue having ROM protein is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the subject. The dosage of monoclonal antibody can vary from about 0.001 $mg/m^2$ to about 500 $mg/m^2$, preferably 0.1 $mg/m^2$ to about 200 $mg/m^2$, most preferably about 0.1 $mg/m^2$ to about 10 $mg^2/m$. Such dosages may vary, for example, depending on whether multiple injections are given, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 key range, which may be readily detected by conventional gamma cameras.

For in vivo diagnosis, radioisotopes may be bound to immunoglobulin either directly or indirectly by using an intermediate functional group. Intermediate functional groups which often are used to bind radioactive metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}In$, $^{97}Ru$, $^{67}Ga$, $^{68}Ga$, $^{72}As$, $^{89}Zr$, $^{201}Tl$, and $^{99m}Tc$.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}Gd$, $^{55}Mn$, $^{162}Dy$, $^{52}Cr$, and $^{56}Fe$.

The monoclonal antibodies of the invention can be used to monitor the course of amelioration of Spirochaetales associated disorder. Thus, by measuring the increase or decrease of antibodies to ROM protein antigen present in various body fluids or tissues, it would be possible to determine whether a particular therapeutic regiment aimed at ameliorating the disorder is effective.

The materials for use in the method of the invention are ideally suited for the preparation of a kit. Such a kit may comprise a carrier means being compartmentalized to receive in close confinement one or more container means such as vials, tubes, and the like, each of the container means comprising one of the separate elements to be used in the method. For example, one of the container means may comprise a Spirochaetales ROM protein binding reagent, such as an antibody. A second container may further comprise ROM proteins or fragments. The constituents may be present in liquid or lyophilized form, as desired.

Monoclonal antibodies are made from antigen containing fragments of the protein by methods well known in the art (Kohler, et al., supra, 1975). The term "antibody" as used in this invention is meant to include intact molecules as well as fragments thereof, such as Fab and $F(ab')_2$, which are capable of binding the epitopic determinant as well as genetically engineered antibody molecules such as single chain, chimeric, CDR grafted antibodies, and variants thereof known to those skilled in the art.

The antibodies of the invention can be used in immunoaffinity chromatography for the isolation of protein fragments and amino acid sequences in ROM proteins containing antigenic activity of the present invention. One way to utilize immunoaffinity chromatography can be utilized is by the binding of the antibodies of the invention to CNBr-Sepharose-4B or Tresyl activated Sepharose (Pharmacia). These solid phase-bound antibodies can then be used to specifically bind sequences containing the antigenic activity of ROM proteins from mixtures of other proteins to enable isolation and purification thereof. Bound sequences can be eluted from the affinity chromatographic material using techniques known to those of ordinary skill in the art such as, for example, chaotropic agents, low pH, or urea.

The invention provides polynucleotides encoding the isolated ROM proteins, preferably those of the genus Treponema, most preferably the ROM proteins of *T. pallidum* shown in Table 1 above. These polynucleotides include DNA, cDNA and RNA sequences which encode ROM proteins or antigenic fragments thereof. It is understood that all polynucleotides encoding all or a portion of ROM proteins are also included herein, so long as they encode a polypeptide with antigenic activity. Such polynucleotides include both naturally occurring and intentionally manipulated polynucleotides. For example, a ROM protein may be subjected to site-directed mutagenesis. The polynucleotides of the invention include sequences that are degenerate as a result of the genetic code. There are only 20 natural amino acids, most of which are specified by more than one codon. Therefore, as long as the amino acid sequence of the ROM protein is unchanged, or although changed retains the antigenic activity of the corresponding ROM protein, all degenerate nucleotide sequences are included in the invention.

As used herein the term "antigenic activity" shall mean the protein or polypeptide binds with suitable affinity under physiologic conditions to an antibody known in the art to be associated with the disease state caused by the pathogen from which the ROM protein or polypeptide is derived. Alternatively, "antigenic activity" means that the protein or polypeptide binds with such affinity to an antibody specific to a Spirochaetaceae ROM protein isolated by the method of the present invention. DNA sequences of the invention can be isolated by several techniques known in the art. These include, but are not limited to: 1) hybridization of probes to genomic or cDNA libraries to detect shared nucleotide sequences, and 2) antibody screening of expression libraries to detect shared structural features.

Screening procedures which rely on nucleic acid hybridization make it possible to isolate any gene sequence from any organism, provided the appropriate probe is available. For example, oligonucleotide probes, which correspond to a part of the sequence encoding the protein in question, can be synthesized chemically. This requires that short, oligopeptide stretches of amino acid sequence must be known, preferably of at least 17 nucleotides in length. The DNA sequence encoding the protein can be deduced from the genetic code, however, the degeneracy of the code must be taken into account. It is possible to perform a mixed addition reaction when the sequence is degenerate. This includes a heterogenous mixture of denatured double-stranded DNA. For such screening, hybridization is preferably performed on either single-stranded DNA or denatured double-stranded DNA. This is especially useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by hybridization of the target DNA to the single probe in the mixture which is its complement (Wallace, et al., *Nucleic Acid Research,* 9:879, 1981).

A cDNA expression library, such as λgtll, can be screened indirectly for ROM polypeptides having at least one antigenic epitope, using antibodies specific for a ROM protein isolated from live pathogen according to the method of this invention or antibodies from the blood of individuals infected with the pathogen of interest previously identified as specific to the pathogen of interest. Such antibodies can be either monoclonal or polyclonal and used to detect an expression product indicative of the presence of a ROM cDNA.

A ROM protein cDNA library can also be screened by injecting different cDNAs into oocytes. After expression of the cDNA gene products occurs, the presence of the specific cDNA gene product can be identified by antibody screening with antibody specifically immunoreactive with ROM polypeptides, for example. Alternatively, functional assays for ROM proteins of toxicogenic activity could be performed to identify ROM proteins producing oocytes.

Specific DNA sequences encoding Spirochaetales ROM proteins can also be obtained by: (1) isolation of double-stranded DNA sequences from genomic DNA; (2) chemical manufacture of a DNA sequence to provide the necessary codons for the polypeptide of interest; and (3) in vitro synthesis of a double-stranded DNA sequence by reverse transcription of mRNA isolated from a eukaryotic donor cell, resulting in a cDNA, or complimentary DNA.

Synthesis of DNA sequences is frequently the method chosen when the entire sequence of amino acid residues of the desired polypeptide product is known. When the entire sequence of amino acid residues of the desired polypeptide is not known, the direct synthesis of DNA sequences is not possible, and the method of choice is the formation of cDNA sequences. Among the standard procedures for isolating cDNA sequences of interest is the formation of plasmid or bacteriophage based cDNA libraries in which mRNA is reverse transcribed from donor cells with a high level of genetic expression. When used in combination with polymerase chain reaction (PCR) technology, less common mRNA species (cDNA) can be cloned as well. When significant portions of the amino acid sequence of a polypeptide are known, labeled single or double-stranded DNA or RNA probes which represent a sequence present in the target cDNA, may be used in DNA/DNA hybridization procedures which are performed on cloned copies of the cDNA, which have been denatured into a single-stranded form (Jay, et al., *Nucleic Acid Research,* 11:2325, 1983).

Since the novel DNA sequences of the invention encode a unique sequence of ROM protein, it is now a routine matter to prepare, subclone, and express smaller polypeptide fragments of DNA from this or corresponding DNA sequences. Alternatively, by utilizing a DNA fragment, it is possible, in conjunction with known techniques, to determine the DNA sequences encoding an entire ROM antigenic protein. Such techniques are described in U.S. Pat. Nos. 4,394,443 and 4,446,235, which are incorporated herein by reference.

The polypeptide resulting from expression of a DNA sequence of the invention can be further characterized as being free from association with other eukaryotic polypeptides or other contaminants that might otherwise be associated with the ROM protein in its natural cellular environment. Isolation and purification of microbially expressed polypeptides provided by the invention may be by conventional means including, preparative chromatographic separations and immunological separations involving monoclonal and/or polyclonal antibody preparation.

For purposes of the present invention, ROM polypeptides that are homologous to those of the invention can be identified by structural as well as functional similarity. Structural similarity can be determined, for example, by assessing polynucleotide strand hybridization or by screening with antibody, especially a monoclonal antibody, which recognizes a unique epitope present on a ROM protein disclosed in this invention. When hybridization is used as criteria to establish structural similarity, those polynucleotide sequences that hybridize under stringent conditions to the polynucleotides of the invention are considered to be essentially the same as the polynucleotide sequences of the invention.

A wide variety of ways are available for introducing a polynucleotide expressing a Spirochaetales ROM protein into the microorganism host under conditions which allow for stable maintenance and expression of the gene. DNA constructs are available which include the transcriptional and translational regulatory signals for expression of the ROM polynucleotide; the ROM gene under their regulatory control, and a DNA sequence homologous with a sequence in the host organism, whereby integration will occur; and/or a replication system which is functional in the host, whereby integration or stable maintenance will occur.

The transcriptional initiation signals will include a promoter and a transcriptional initiation start site. In some instances, it may be desirable to provide for regulative expression of the ROM polynucleotide. This can be achieved with operators or a region binding to an activator or enhancers that are capable of induction upon a change in the physical or chemical environment of the host. For example, a temperature sensitive regulatory region may be employed where the organisms may be grown up in the laboratory without expression of the ROM protein, but upon change in the growth conditions or environment, expression would begin. Other techniques may employ a specific nutrient medium in the laboratory, which inhibits the expression of the ROM protein, where the nutrient medium in the later environment would allow for expression of the ROM protein. For translational initiation, a ribosomal binding site and an initiation codon will be present.

Various manipulations may be employed for enhancing the expression of the mRNA, particularly by using an active promoter, as well as by employing sequences, which enhance the stability of the mRNA. The initiation and translational termination region will involve stop codon(s), a terminator region, and optionally, a polyadenylation signal.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the expression construct during introduction of the DNA into the host.

A marker structural gene may be present that provides for selection of those hosts that have been modified or transformed. The marker will normally provide for selective advantage, for example, providing for biocide resistance, for example, resistance to antibiotics or heavy metals; complementation, so as to provide prototropy to an auxotrophic host, or the like.

Where no functional replication system is present, the construct will also include a sequence of at least 50 basepairs (bp), preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the ROM protein gene will be in close proximity to the gene providing for complementation as well as the gene providing for the competitive advantage. Therefore, in the event that a ROM protein gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the Tac promoter, the naturally-occurring promoters associated with the ROM protein gene, where functional in the host. See, for example, U.S. Pat. Nos. 4,332,898, 4,352,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed that has a replication system that is functional in the host. The replication system may be derived from the chromosome, an episomal element normally present in the host or a different host, or a replication system from a virus that is stable in the host. A large number of plasmids are available, such as pBR322, pACYC184, RSFIOIO, pR01614, and the like (see, for example Olson, et al., *J. Bacteriol.* 150:6069, 1982, and Bagdasarian, et al., *Gene*, 16:237, 1981, and U.S. Pat. Nos. 4,356,270, 4,362,817, and 4,371,625.)

The ROM polynucleotide can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, as described above. Where integration is desired, the plasmid will desirably include a sequence homologous with the host genome.

The transformants can be isolated in accordance with conventional techniques usually employing selection of the desired organism as against unmodified organisms or transferring organisms, when present. The transformants then can be screened for pesticidal activity.

As hosts, of particular interest will be the prokaryotes and the lower eukaryotes, such as fungi. Illustrative prokaryotes, both Gram-negative and -positive, include Enterobacteriaceae, such as Escherichia, Ervinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., and the like. Specific organisms include *Pseudomonas aeruginosa, Pseudomonas fluorescens, Saccharomyces cerevisiae, Bacillus thuringiensis, Escherichia coli, Bacillus subtilis,* and the like.

In general, expression vectors containing promotor sequences which facilitate the efficient transcription of the inserted genetic sequence are used in connection with the host. As described above, biologically functional viral or plasmid DNA vectors capable of expression and replication in a host are known in the art. Such vectors are used to incorporate ROM protein encoding DNA sequences of the invention. Expression vectors typically contain an origin of replication, a promoter, and a terminator, as well as specific genes that are capable of providing phenotypic selection of the transformed cells.

Transformation of the host cell with the recombinant DNA may be carried out by conventional techniques well known to those skilled in the art. Where the host is prokaryotic, such as *E. coli*, competent cells which are capable of DNA uptake can be prepared from cells harvested after exponential growth and subsequently treated by the $CaCl_2$ method using procedures well known in the art. Alternatively, $MgCl_2$ or RbCl could be used.

Where the host used is a eukaryote, various methods of DNA transfer can be used. These include transfection of DNA by calcium phosphate-precipitates, conventional mechanical procedures such as microinjection or electroporation, insertion of a plasmid encased in liposomes, or the use of viral vectors.

Eukaryotic host cells may also include yeast. For example, DNA can be expressed in yeast by inserting the DNA into appropriate expression vectors and introducing the product into the host cells. Various shuttle vectors for the expression of foreign genes in yeast have been reported (Heinemann, J. et al., *Nature*, 340:205, 1989; Rose, et al., *Gene*, 60:237, 1987).

Isolation and purification of microbially expressed protein, or fragments thereof provided by the invention, may be carried out by conventional means including preparative chromatography and immunological separations involving monoclonal or polyclonal antibodies. Antibodies provided in the present invention are immunoreactive with the Spirochaetales ROM proteins of the invention. Antibody which consists essentially of pooled monoclonal antibodies with different epitopic specificities, as well as distinct monoclonal antibody preparations are provided. Monoclonal antibodies are made from antigen containing fragments of the ROM protein by methods well known in the art (Kohler, et al., supra, 1975; *Current Protocols in Molecular Biology*, Ausubel, et al., ed., 1989).

Minor modifications of the ROM protein primary amino acid sequence may result in polypeptides that have substantially equivalent antigenic activity compared to the ROM proteins and polypeptides described herein. Such modifications may be deliberate, as by site-directed mutagenesis, or may be spontaneous. All proteins produced by these modifications are included herein as long as the antigenic activity for antibodies specific to ROM proteins is present.

The composition of the amino acids of the ROM proteins of this invention can be determined by methods well known in the art, for instance, the Phenylthiohydantoine (PTH) method of Edman, et al. (Europ. *J. Biochem.*, 1:30, 1967). Briefly, in this method the purified protein is dried under vacuum and redissolved in a small volume of acetonitrile 95% plus TFA (0.08%). The concentrated sample is then introduced into a gaseous phase sequencer connected to a phenylthiohydantoine (PTH) analyzer. From the amino acid sequence so obtained, a DNA sequence encoding the protein can be deduced using routine methods well known in the art.

Alternatively, to discover the nucleotide sequence of DNA material obtained using the methods of this invention, double stranded dideoxy sequencing can be performed, for example on a DuPont Genesis 2000, using the DuPont Genesis 2000 sequencing kit according to the manufacturer's instructions. Post gel processing can be done with the Base Caller 5.0 program (DuPont, Boston, Mass.). Alternatively, a DNA sequence of the clone can be obtained using a Sequenase® II kit (United States Biochemical, Cleveland, Ohio) on the automated DNA sequencer Genesis 2000 (Dupont, Wilmington, Del.) according to the manufacturer's instructions. The DNA encoding the gene may also be chemically synthesized (Merrifield, *J. Am. Chem. Soc.*, 85 pp. 2149 (1963)), or generated by PCR.

The following examples illustrate the manner in which the invention can be practiced. It is understood, however, that the examples are for the purpose of illustration and the invention is not to be regarded as limited to any of the specific materials or conditions therein.

EXAMPLE 1

Source of Treponemes

*T. pallidum*, subsp. pallidum, Nichols strain, was maintained by testicular passage in New Zealand White rabbits as described previously (Miller, et al., *Br. J. Vener. Dis.*, 39:195, 1963). Animals used to prepare *T. pallidum* outer membrane and antigen for sodium dodecyl sulfate (SDS)-polyacrylamide gel electrophoresis (PAGE) were injected intramuscularly with 10 mg of cortisone acetate (Merck Sharp & Dohme, Rahway, N.J.) per kg of body weight from days 3 through 12 after infection.

*T. vincentii* was grown in spirolate broth (Gibco) supplemented with 10% heat-inactivated rabbit serum. Approximately 300 ml of culture containing $2\times10^8$ organisms/ml was centrifuged at 10,000× g for 15 min. The resulting treponemal pellet was resuspended in 140 ml of phosphate buffered saline (PBS), pH 7.2, and used for outer membrane isolations or recentrifuged as described for use as antigen in SDS-PAGE.

Purification of *T. pallidum*

A total of 300 ml of PBS, pH 7.2, in 50 ml volumes was used to extract treponemes from 20 infected rabbit testicles. The treponemal suspension, containing approximately $6\times10^{10}$ organisms was subjected to two low speed centrifugations at 4000× g in order to remove gross tissue debris. Treponemes were then pelleted by centrifugation at 20K × g for 15 min followed by resuspension in 40 ml of PBS containing 0.5% Bovine serum albumin (BSA; Intergen Co., Purchase, N.Y.) and 7% FICOLL™ density gradient separation medium (Pharmacia, Piscataway, N.J.). Ten milliliters (10 ml) of suspension was layered onto 25 ml of a discontinuous Ficoll/PBS gradient with increasing buoyant densities of 1.045, 1.055, 1.065, and 1.075, and 1.085 g/ml. After centrifugation at 7K × g for 15 min, several bands were observed in the gradient. Previous studies using darkfield and electron microscopy of the four interdensity zones have shown "clean" single treponemes within the two upper zones (1.065–1.055 and 1.055–1.045) and some clumped and single treponemes plus host cell debris within the two lower zones (1.085–1.075 and 1.075–1065). Only treponemes recovered from the uppermost zone gradient by needle aspiration, followed by a 4-fold dilution in PBS, were used for subsequent experiments. The resulting treponemal suspension was used immediately for extraction of the outer membrane.

EXAMPLE 2

Isolation of *T. pallidum* and *T. vincentii* Outer Membrane

Figure 1B:
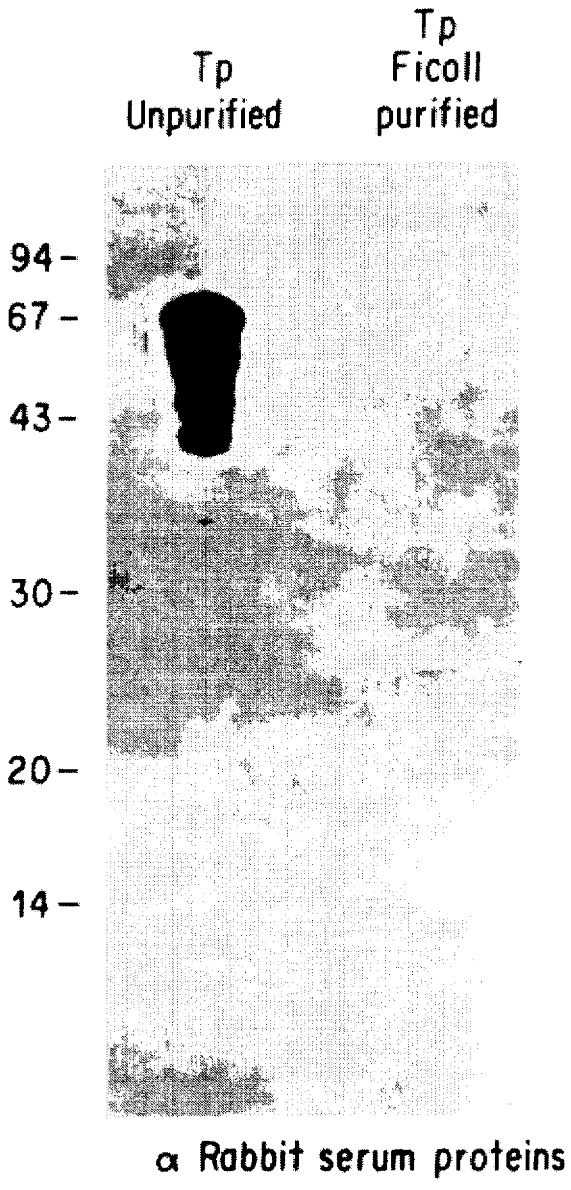

To 140 ml of treponemal suspension obtained in Example 1 containing approximately $5\times10^{10}$ treponemes was added 200 ul of R18 octyl-decyl Rhodamine chloride (Molecular Probes, Inc., Eugene, Oreg.). The suspension was incubated at room temperature for 10 min and then centrifuged at 8K × g for 20 min. For removal of the outer membrane, the treponemal pellet was resuspended into 60 ml of ice cold 0.05M sodium citrate buffer, pH 3.2, and incubated on a rocker with occasional vortexing for 2 hrs at room temperature to release the outer membrane from the inner membrane. The suspension was then centrifuged three times at 8K × g for 15 min in order to remove treponemal protoplasmic cylinders. The supernatant containing released outer membrane was then neutralized using 1M Tris-HCl, pH 9.0, and centrifuged at 150K × g for 16 hrs at 15° C. The resulting membrane pellet was resuspended into 2 ml of PBS, layered onto 36 ml of a continuous 5–40% sucrose/PBS gradient for *T. pallidum* or 10–40% gradient for *T. vincentii*, and centrifuged at 100K × g for 16 hrs at 15° C. Following centrifugation, the outer membrane band, identified visually by Rhodamine labeling, was needle aspirated, diluted 7-fold with PBS, and recentrifuged at 150K g for 5 hr. The final purified membrane pellet was resuspended in 100 ul of PBS containing 1 mM EDTA, 1 mM PMSF, and stored at 4° C. As shown in FIG. 1B, the citrate buffer treated organisms showed release of outer membrane.

EXAMPLE 3

Electron Microscopy (EM) and Freeze-Fracture EM

Figure 2A:
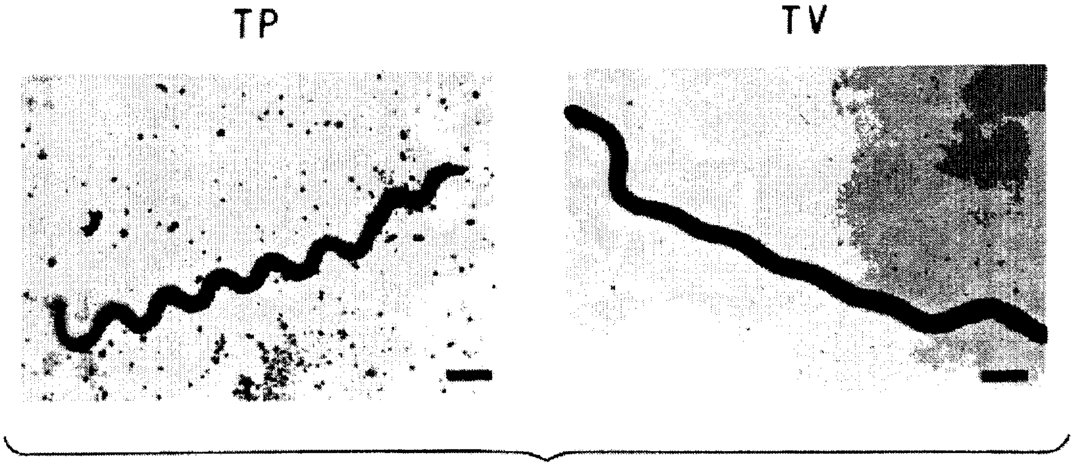

For electron microscopy, a PARLODION® grid film cover (Mallinckrodt, Inc., St. Louis, Mo.) and carbon-coated 300-mesh copper grids (Ted Pella, Inc., Redding, Calif.) were floated for 5 min on 40 ul specimen drops. After 3 washes in PBS and 2 washes in double-distilled water, the grids were negatively stained with 1% uranyl acetate and examined in an electron microscope (JEOL 100 CX) at 80 kV accelerating voltage. Freeze-fracture EM of outer membrane vesicles was performed as follows. Fifty microliters (50 ul) of membrane suspension was pelleted by centrifugation at 200K × g for 3 hrs and resuspended in 1 ul of 20% glycerol in double-distilled water. A 0.5 ul sample was placed on a standard Balzars specimen holder (Balzars Co., Redding, Calif.) and frozen by immersion in liquid propane (−190° C.) using a guillotine-type device. Frozen samples were transferred under liquid nitrogen to the specimen stage of a Balzars 400K freeze-fracture apparatus precooled to −150° C. Frozen samples were fractured at −120° C. by using a knife cooled at the temperature of liquid nitrogen. The fracture surface was immediately replicated with platinum-carbon at 45° C. and carbon at 90° C. The replicas were floated in 3–4% sodium hypochlorite to bleach the organic material and washed three times in double-distilled water. The replicas were then placed on Formvar-coated freeze-fracture grids (Ted Pella, Inc.) and observed by electron microscopy as described above. The electron micrograph shown in FIG. 2D shows few intramembranous protein particles.

EXAMPLE 4

Isolation of ROMs from Outer Membrane Using One and Two Dimensional SDS-PAGE SDS-polyacrylamide slab gels were run by using the discontinuous buffer system of Laemmli (Laemmli, Nature, London, U.K., 227:680–685, 1970). Samples containing $5\times10^8$ whole organisms or 1 to $5\times10^9$ treponemal equivalents of membrane material were boiled for 10 min in final sample buffer containing 4% SDS, 10% 2-mercaptoethanol, and 0.01% bromphenol blue in 62.5 mM Tris buffer, pH 6.8 (FSB); for some samples, urea at a final concentration of 8M (FSB-U) was included. In some experiments, samples were solubilized in FSB containing proteinase K (Sigma Chemical Co., St. Louis, Mo.) at a concentration of 100 ug/ml and incubated for 1 hr at 37° C. before boiling. Two-dimensional gel electrophoresis was performed as described by O'Farrell (*J. Biol. Chem.*, 250:4007–4021, 1975) with minor modifications. Outer membrane material containing from $5\times10^9$ to $3\times10^{10}$ treponemal equivalents was first solubilized for 1 hr at room temperature in lysis buffer containing 9M urea, 2% Nonidet P-40 (NP40) (Sigma Chemical Co., St. Louis, Mo.) and 2% carrier ampholytes at pH 9.5. Isoelectric focusing was carried out for 18 hrs at a constant voltage of 600v in 0.2 cm×12 cm tube gels containing 2% pH 5–7 and 0.8% pH 3–10 Ampholines (BioRad, Richmond Calif.), 2% NP40, and 9M urea. The second dimension consisted of standard SDS-PAGE as described above. After electrophoresis, gels were stained with Coomassie brilliant blue or transferred to polyvinylidene defluoride (PVDF) membranes (Millipore, Bedford, Mass.) as previously described (Towbin, et al., *Proc. Natl. Acad. Sci. USA*, 76:4350–4354, 1979). Following transfer, PVDF membranes were stained with 1% Amido Black or Aurogold Forte (Amersham, UK). For immunoblotting, PVDF membranes were incubated for 1 hr with serum diluted 1:1000 in PBS containing 5% nonfat dry milk (Carnation Co., Los Angeles, Calif.) and 0.1% Tween-20 (Sigma Chemical Co., St. Louis, Mo.) (MT-PBS). Antibody-antigen binding was detected using the enhanced chemiluminescence (ECL) system of Amersham (Amersham, UK). Blots were incubated for 1 hr in anti-rabbit Ig or anti-mouse Ig conjugated to horseradish peroxidase diluted 1:2500 in MT-PBS. Blots were next washed in PBS containing 0.1% Tween-20, incubated for 1 min in the ECL developing reagents (Amersham, UK), and then autoradiographed with Kodak X-AR5 film. The Coomassie stained gel is shown in FIG. 1A, and the PVDF immunoblot is shown in FIG. 1B.

EXAMPLE 5

Detection of *T. pallidum* Penicillin Binding Proteins

Penicillin binding proteins (PBPs) of *T. pallidum* were identified using $^{125}$Iodine-labeled penicillin-V as follows. Sodium (trimethylstannyl)phenoxyacetamidopenicillin (Lilly Laboratories, Eli Lilly and Company, Indianapolis, Ind.), was labeled with Na$^{125}$Iodine using chloramine-T as previously described (Preston, et al., *Antmicrob. Agents Chemother.*, 34:718–721, 1990). Equal volumes of $^{125}$I-penicillin-V were combined with $1\times10^8$ Ficoll purified *T. pallidum*, $1\times10^8$ *T. pallidum* protoplasmic cylinders, and $5\times10^9$ treponemal equivalents of outer membrane. Suspensions were incubated at room temperature for 30 minutes prior to centrifugation at 10K × g for 15 minutes for whole organisms and protoplasmic cylinders, and at 100K × g for 1 hr for outer membrane material. Pellets were resuspended in FSB and electrophoresed by the SDS-PAGE, using conditions described above. Following electrophoresis, the gel was vacuum dried and then autoradiographed with Kodak X-AR5 film at room temperature for 24 hrs. The results are shown in FIG. 4.

EXAMPLE 6

Preparation of Antisera from Syphilitic Rabbits

Serum from syphilitic rabbits immune to challenge (immune rabbit serum; IRS) was acquired 6 months post-infection intratesticularly with 4×10 *T. pallidum*. Antiserum against the *T. pallidum* recombinant 4D protein was prepared as described previously (Radolf, et al., supra., 1986).

Monoclonal antibodies against the *T. pallidum* 47-kDa lipoprotein (MAb llE3) and against the 42-kDa TmpA lipoprotein were kindly provided by Dr. Michael V. Norgard, University of Texas (Chamberlain, et al., supra., 1989) and Drs. Jan vanEmben and Leo Schouls, University of Bilthoven, Netherlands (Schouls, et al., *Microb. Pathog.*, 7:175–188, 1989), respectively. Anti-rabbit serum proteins were purchased from Sigma Chemical Co., St. Louis, Mo.

EXAMPLE 7

Preparation of Control Antisera

Antiserum against *T. vincentii* was generated in rabbits as follows. Approximately $1\times10^9$ PBS washed *T. vincentii* organisms were disrupted by sonication, combined with Freund's complete adjuvant, and injected both intramuscularly (IM) and subcutaneously (SC). After 3 weeks, animals were boosted IM and SC using a similarly prepared suspension in Freund's incomplete adjuvant. Animals were bled one week following the boost immunization.

EXAMPLE 8

Isolation of the *T. pallidum* and *T. vincentii* outer Membrane

The present outer membrane isolation procedure comprises the use of several novel steps including (1) a Ficoll gradient to purify *T. pallidum*, octyl-decyl rhodamine to label membranes, (2) use of a lipid-soluble dye marker, preferably a fluorescent dye marker that intercalates into the outer membrane and (3) a low ionic strength and low pH buffer for the selective removal of the outer membrane.

Figure 2B:
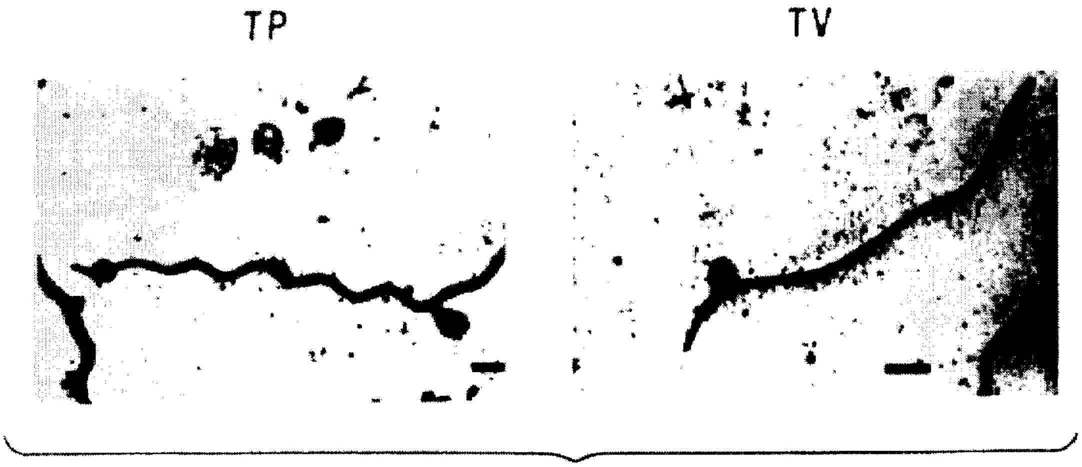

Ficoll purification of *T. pallidum* resulted in significant removal of host contaminating proteins as determined by SDS-PAGE as shown in FIG. 1A, and immunoblotting using anti-rabbit whole serum, as shown in FIG. 1B. Ficoll purified *T. pallidum* and PBS washed *T. vincentii* were treated with 0.05M Citrate buffer which resulted in the release of membrane as monitored by fluorescent microscopy of rhodamine labeled material (data not shown) and by electron microscopy as shown in FIG. 2B. After 45 mins, the majority of treponemes had significantly narrower diameters consistent with the removal of their outer membranes. The absence of endoflagellar filaments, which are dissociated to flagellin at low pH (Blanco, et al., supra., 1988), may have also contributed to the release of outer membrane material. Comparison by SDS-PAGE of the protoplasmic cylinders from citrate treated treponemes with those of whole treponemes showed a similar profile and intensity of stained proteins (data not shown) indicating that treponemes were not disrupted by this procedure.

Sucrose gradient purification of membrane material yielded a single rhodamine labeled band at the 7% sucrose gradient for *T. pallidum* and at the 35% sucrose gradient for *T. vincentii* as determined by refractive index analysis (data not shown). The membrane nature of this material was demonstrated by electron microscopy, which showed membrane vesicles that ranged in diameter from approximately 300 to 700 nm as shown in FIG. 2C.

EXAMPLE 9

Freeze-Fracture Electron Microscopy of Membrane Vesicles

Purified membrane vesicles were analyzed by freeze-fracture electron microscopy in order to determine intramembranous particle composition as shown in FIG. 2D. Membrane vesicles from both *T. pallidum* and *T. vincentii* contained extremely few protein particles. Of 200 *T. pallidum* vesicles observed, only 8 were found to have fracture faces containing particles; the number of particles in these fracture faces ranged from 1 to 3. By comparison, of 50 *T. vincentii* vesicles observed, 22 had fracture faces containing at least 1 particle. Total particle enumeration showed that the membrane particle density of *T. pallidum* was approximately six times less than that of *T. vincentii*. In contrast, the fraction faces of *T. pallidum* and *T. vincentii* protoplasmic cylinder inner membranes and of host tissue membranous material acquired from noninfected rabbits contained a relatively high density of particles (data not shown).

Composition of *T. vincentii* Outer Membrane Vesicles

Figure 3:
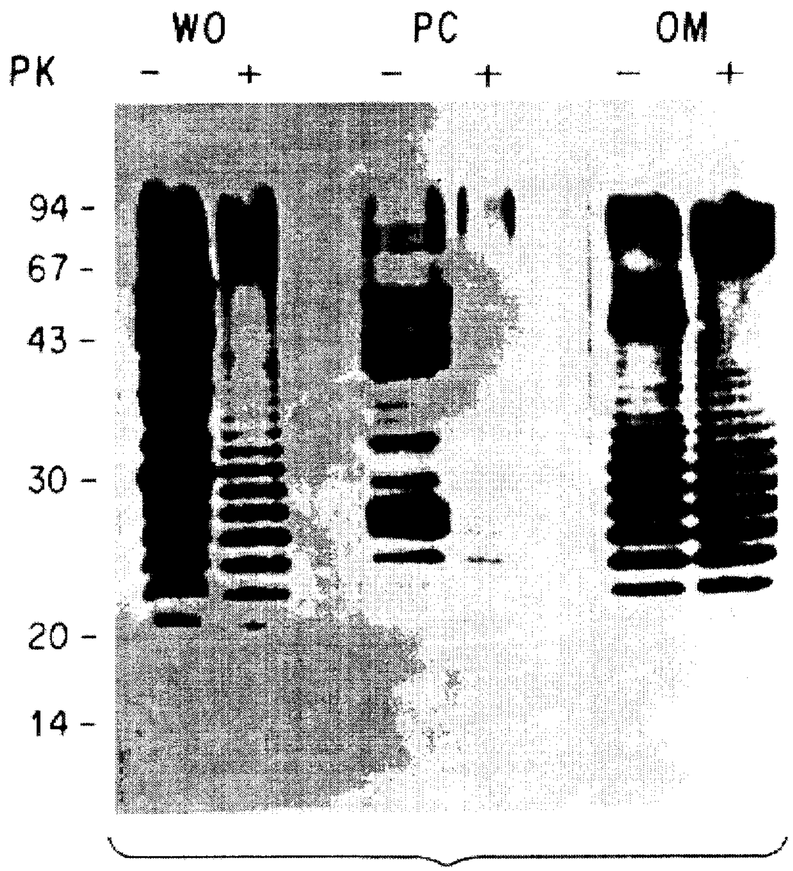
FIG. 3 shows an immunoblot analysis of *T. vincentii*, untreated and treated with proteinase K (PK), showing $2\times10^8$ equivalents of whole organisms (WO) and protoplasmic cylinders (PC) and $1\times10^9$ equivalents of outer membrane (OM). The molecular weights ($\times10^3$) of marker standards are indicated.

The detection of the *T. vincentii* LPS stepladder by immunoblot analysis of proteinase K (PK) treated membrane, protoplasmic cylinder, and whole organism fractions was used to assess the efficiency of outer membrane recovery. As shown in FIG. 3, the number and intensity of LPS bands detected from $1\times10^9$ equivalents of outer membrane material was similar to that of $2\times10^8$ equivalents of whole organisms. By comparison, $2\times10^8$ equivalents of protoplasmic cylinders showed a marked decrease in the number and intensity of its LPS stepladder bands. These results indicate that approximately 20% of the *T. vincentii* outer membrane was recovered.

Immunoblots of the *T. vincentii* outer membrane untreated with PK probed with antisera generated against whole organisms as described in Example 6 above and Coomassie stained SDS-PAGE (data not shown) also detected two antigenic proteins with molecular masses of approximately 65- and 55-kDa.

Composition of *T. pallidum* Outer Membrane Vesicles

Detection of inner membrane associated penicillin binding proteins (PBPs) was used to assess the purity of isolated outer membrane (Cunningham, et al., supra., 1987; Radolf, et al., supra, 1989). $1\times10^8$ whole *T. pallidum* organism (Tp) and protoplasmic cylinders and $5\times10^9$ equivalents of outer membrane (OM) were incubated with $^{125}$I-labeled penicillin V prior to SDS-PAGE and autoradiography. As shown in FIG. 4, major PBPXs of 94-, 80-, 58-, 43-, and 38-kDa were detected in the whole organism and protoplasmic cylinder preparations but not in the treponemal equivalents of outer membrane material, indicating the absence of inner membrane contamination.

Figure 5:
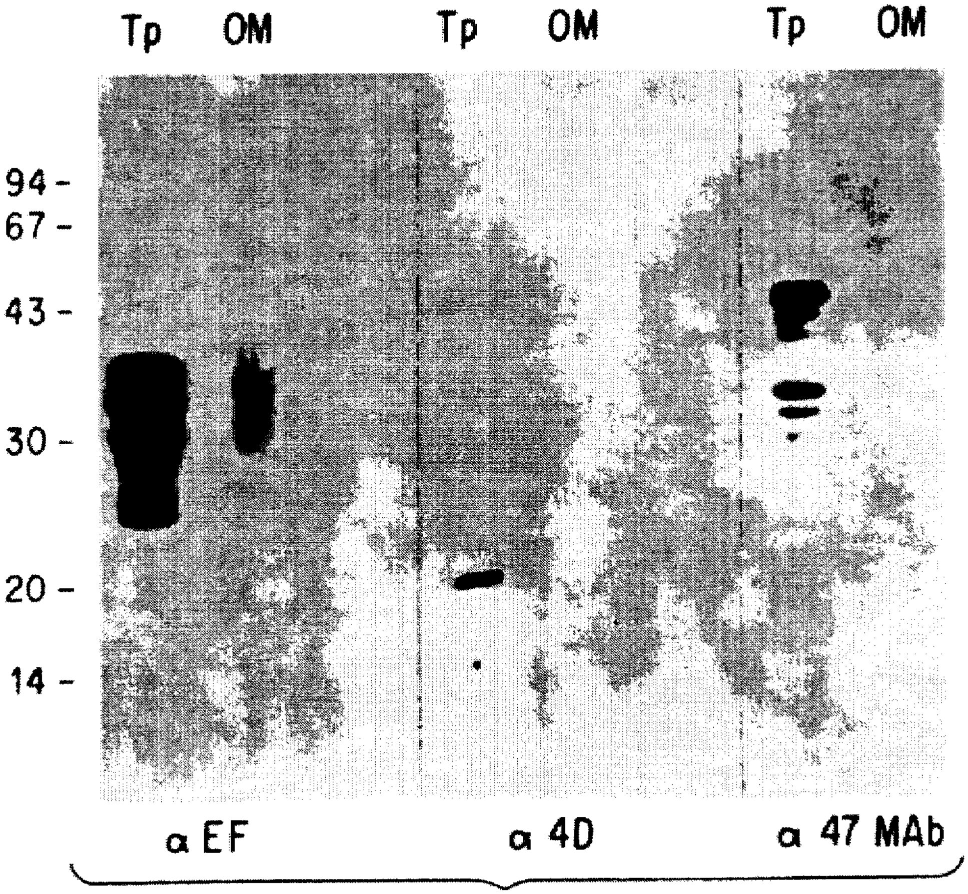
FIG. 5 shows an immunoblot analysis of outer membrane material of *T. pallidum* probed with antisera against three periplasmic associated proteins: whole organisms (Tp), outer membrane (OM) are probed with anti-endoflagellar serum (αEF); anti-19-kDA "4D" serum (α4D); and monoclonal antibody against 47-kDa lipoprotein (α47 MAb). The molecular weights ($\times10^3$) of marker standards are indicated.

In order to determine the extent of periplasmic protein contamination, $5\times10^9$ treponemal equivalents of outer membrane material and $1\times10^8$ whole organisms were probed on immunoblots with specific antiserum against the 19-kDa proplasmic cylinder associated protein 4D (Radolf, et al., supra, 1989), specific antiserum against the endoflagella (Champion, et al., *Infect. Immun.*, 58:3158–3161, 1990), and a monoclonal antibody against the 47-kDa major lipoprotein (Chamberlain, et al., supra, 1989). The results shown in FIG. 5 detect no 47-kDa lipoprotein or 4D protein. Further, only trace amounts of endoflagella were detected, corresponding to approximately 0.2% endoflagellar contamination based upon a 10-fold decrease in the relative intensities of endoflagellar bands detected as compared to those of $1\times10^8$ whole organisms. These findings indicate that the outer membrane preparation was essentially free from contamination by three constituents present in the periplasm of *T. pallidum*.

Figure 6:
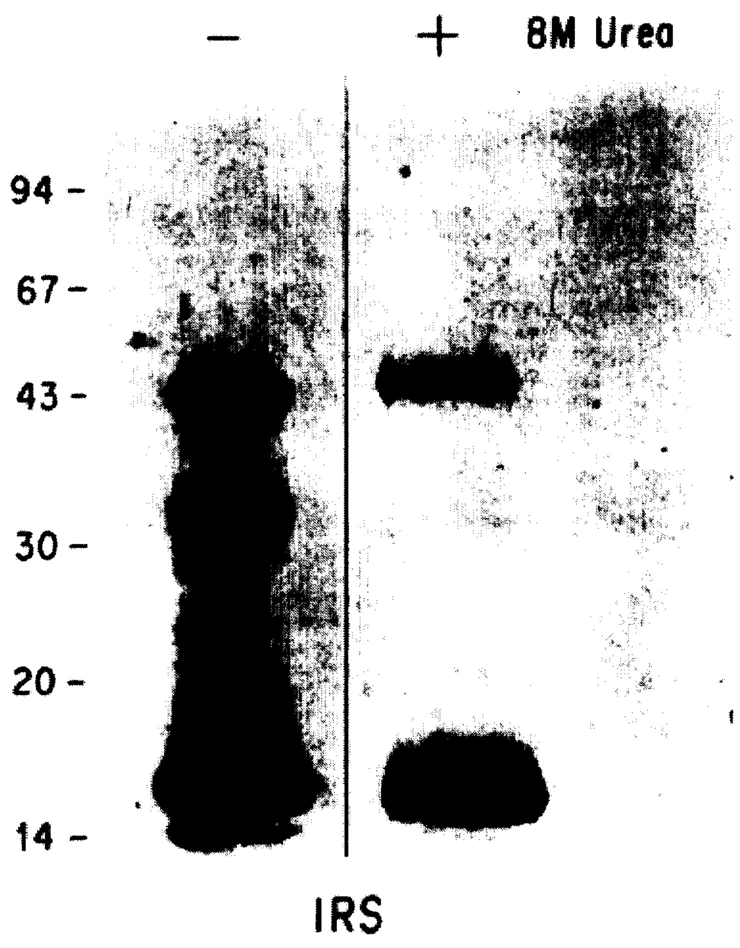
FIG. 6 is an immunoblot showing immune rabbit serum (IRS) detection of *T. pallidum* outer membrane associated proteins. The molecular weights ($\times10^3$) of marker standards are indicated (+indicates treatment with 8M urea).
Figure 7:
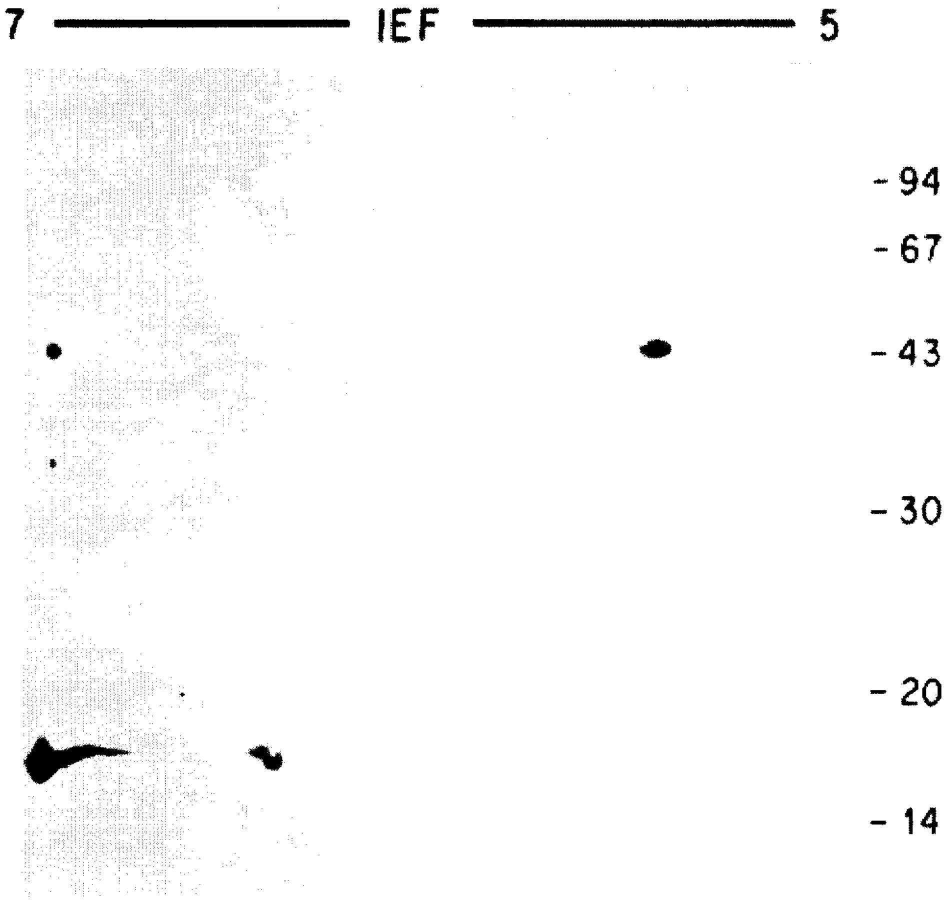
FIG. 7 is an SDS-PAGE immunoblot showing immune rabbit serum (IRS) detection of *T. pallidum* outer membrane associated proteins separated by two dimensional gel electrophoresis. The molecular weights ($\times10^3$) of marker standards are indicated. The isoelectric focus (EIF) range from 7 to 5 is indicated by a bar at the top.

Consistent with the known paucity of outer membrane protein in *T. pallidum* (Radolf, et al., *Proc. Natl. Acad. Sci. USA*, 86:2051–2055, 1989; Walker, et al., supra, 1989) and the above freeze-fracture EM findings, Coomassie stained SDS-PAGE of approximately $5\times10^9$ treponemal equivalents of membrane material failed to detect any major protein bands (data not shown). The initial identification of membrane associated protein was determined antigenically using immune rabbit antisera (IRS) and enhanced chemiluminescence (ECL). The $5\times10^9$ equivalents of *T. pallidum* outer membrane material were prepared in sample buffer, with and without 8M urea, before being probed with IRS. As shown in FIG. 6, three prominently reacting bands at 17-, 32-, and 45-kD were detected in the absence of 8M urea. Solubilization of membrane material in the presence of 8M urea resulted in the loss of the 32-kDa band, but not the 17and 45-kDa proteins, suggesting only two major antigenic species. This finding was confirmed by two dimensional (2D) immunoblot analysis as shown in FIG. 7. The 17-kDa protein had a pI of greater than 7 and showed additional oligomeric forms at 32- and 45-kDa, while the 45-kDa protein showed a single spot at a pI of approximately 5.5. The 45-kDa protein was subsequently identified as the TmpA lipoprotein (Hansen, et al., supra, 1985) using specific monoclonal antibodies (data not shown). Longer exposed autoradiograms of these 2D immunoblots also identified spots corresponding to the pI's of the endoflagellar proteins (data not shown).

Figure 8:
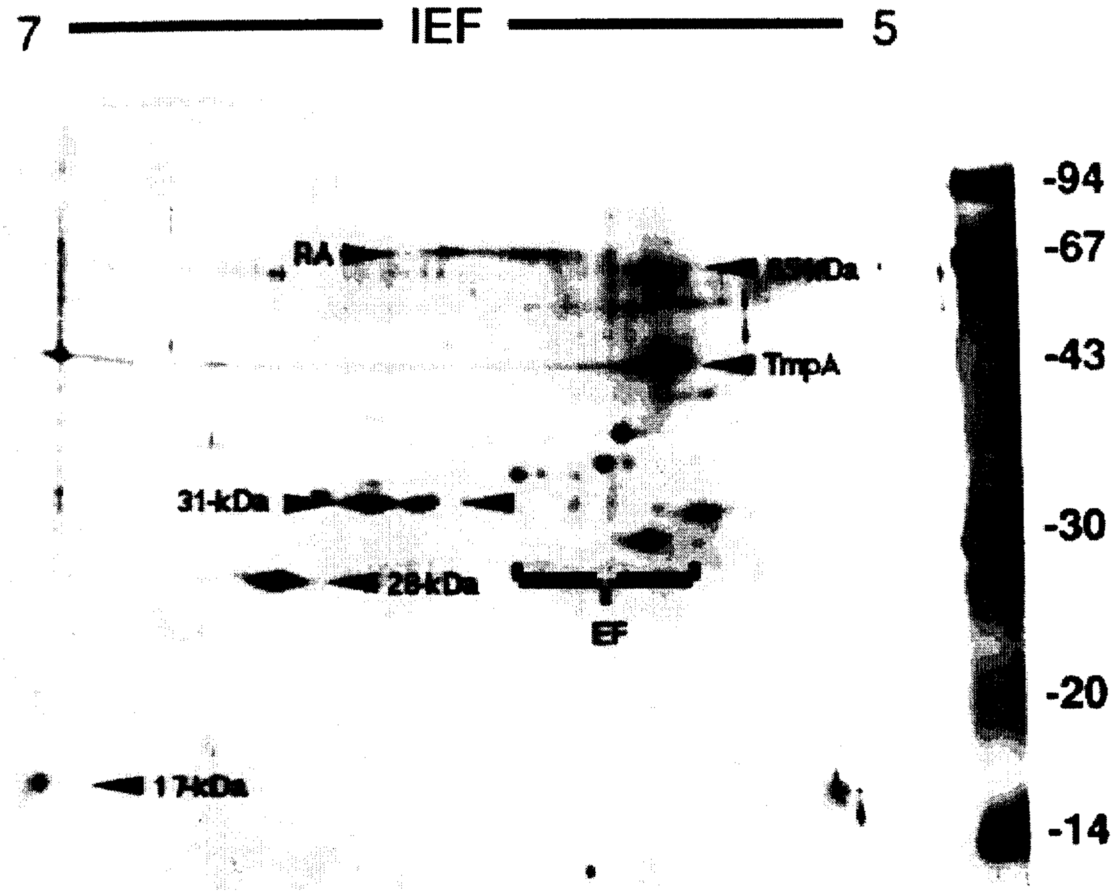
FIG. 8 shows gold staining detection of *T. pallidum* outer membrane associated proteins separated by two dimensional gel electrophoresis. Arrows and bracket indicate *T. pallidum* proteins identified, including endoflagella (EF) and TmpA. The molecular weights ($\times10^3$) of marker standards are indicated. The isoelectric focus (EIF) range from 7 to 5 is indicated by a bar at the top.

In addition to the 17-kda, TmpA, and endoflagellar proteins, gold stained 2D immunoblots of SDS-PAGE gels (shown in FIG. 8) containing $3\times10^{10}$ treponemal equivalents of outer membrane which were subjected to isoelectric focusing (IEF) pH 5 to 7, showed five additional proteins, including two separate spots with different pI's at 31-kDa and single spots at 26-, 65-, and 68-kDa. While the 68-kDa protein was shown by immunoblot analysis to be rabbit albumin, all of the other proteins reacted specifically with low dilutions of IRS, indicating their origin in *T. pallidum* (data not shown).

Figure 9:
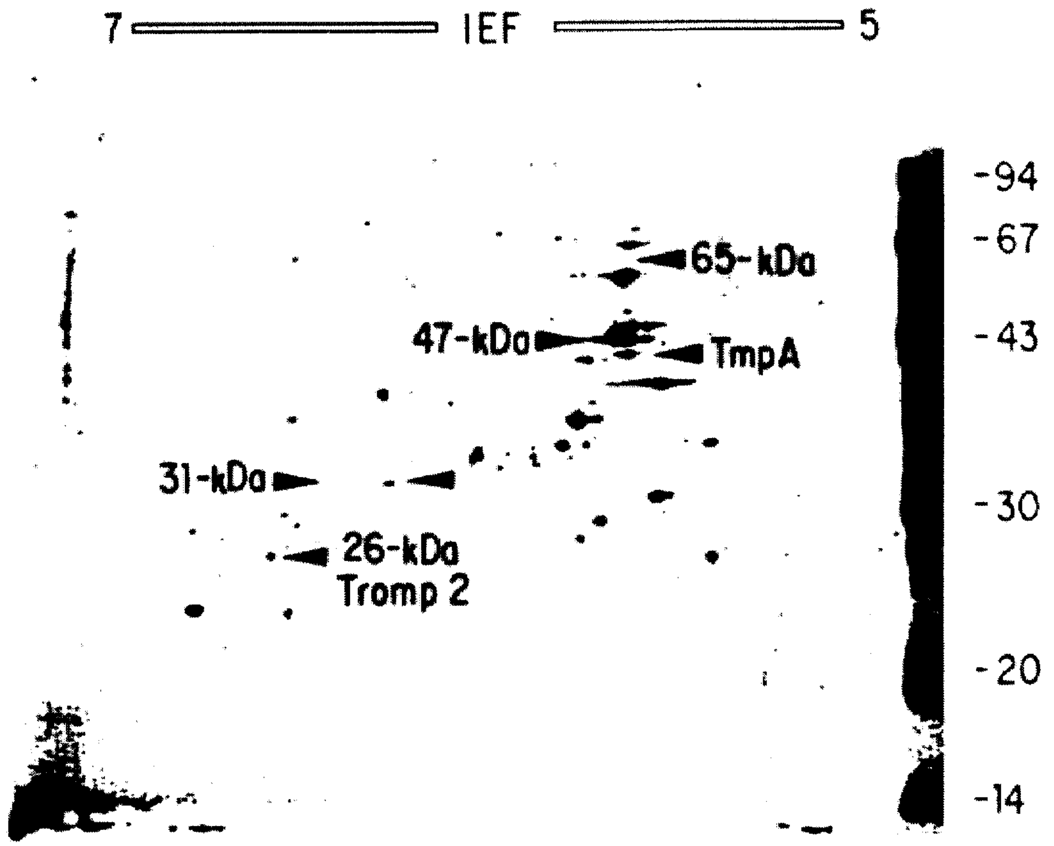
FIG. 9 is an SDS-PAGE immunoblot showing outer membrane proteins separated from $3\times10^{10}$ *T. pallidum*. The native TROMP2 protein (26-kDa) is indicated by an arrow with the label TROMP2 underneath. Molecular masses (in kilodaltons) of prestained protein markers are indicated on the right.

As shown in FIG. 9, outer membrane material from $3\times10^{10}$ organisms were subjected to isoelectric focusing (pH 5 to 7) followed by SDS-PAGE and transferred to a PVDF membrane. Separated proteins from the outer membrane were visualized by being stained with Aurodye Forte dye. The native TROMP2 protein (26-kDa) is indicated by an arrow with the label Tromp2 underneath.

EXAMPLE 10

Cloning of the Tromp1 and Tromp 2 genes

To isolate the Tromp1 gene, two different degenerate mixed oligonucleotides, designated 31-A and 31-C, were made to the amino acid sequence of a tryptic digest amino acid sequence analysis peptide (AHDMQE) and (EEAEFD), respectively, generated from the 31-kda native protein (pI 6.7) obtained from the outer membrane of *Treponema pallidum*. The primers were used in a PCR reaction with the 7 to 9 kb fragment of genomic *T. Pallidum* DNA prepared by digestion with EcoRI. A *T. pallidum* genomic library was made by partially digesting the DNA with EcoRI, AluI, RsaI, and HaeIII. Following digestion, the DNA was purified and EcoRI-adapted. The restriction fragments were subsequently cloned into the λZAP II phage cloning system (Stratagene, San Diego, Calif.) and probed with the PCR product generated using the above described 31-A and 31-C mixed oligonucleotides. From this library, 4 clones, designated 2A, 2B, 3, and 6, were identified with the probe. Following plaque purification, PCR was performed on each phage clone to determine the actual insert size of DNA. The insert size for clones 2A and 3 were both approximately 1600 bp. Clone 2B had an insert size of approximately 1300 bp. The insert size for clone 6 was too large to determine by PCR, but was estimated to be greater than 8 kbp.

Attempts were made to convert all 4 clones into the pBluescript SK(−) plasmid form (Stratagene, San Diego, Calif.) by in vivo excision. However, results of this attempt indicated that clones 2A, 3, and 6 were expressing a product toxic to the *E. coli* cells harboring the plasmids. The indication of toxicity was the very slow rate at which the cells were growing. Upon continued cultivation on solid media, the cells began to lose parts of the insert DNA, upon which subsequent growth became normal.

It was observed that clone 2A appeared to be slightly less toxic than the other two clones. Therefore, this clone was chosen for further analysis. In order to obtain intact recombinant DNA, clone 2A was grown for a very short time on LB agar plate solid media (Gibco BRL, Gaithersberg, Md.) and then cells were scraped off for plasmid DNA preparation. The DNA appeared to be intact based on the insert size of approximately 1600 bp when digested with EcoRI. In order to reduce the toxicity of the protein to the host *E. coli*, the 1600 bp fragment was subsequently restricted into three fragments of approximately 872, 700, and 80 bp by digestion with HindIII. All three fragments were successfully subcloned back into pBluescript plasmid and were no longer toxic to *E. coli*.

The TROMP2 gene was cloned by an analogous procedure in that a mixed oligonucleotide probe was generated based on amino acid sequence analysis following a tryptic digest of the 26-kDa outer membrane protein. The mixed oligonucleotide, designated 26-B, hybridized to a 4.2 kb EcoR1 restriction fragment by Southern blot analysis of *T. Pallidum* genomic DNA. DNA fragments in the size range of 3 to 5 kb were excised from the agarose gel, purified, and ligated into the lambda ZAPII vector (Stratagene) and probed with 26-B. Four positive plaques were identified, replated, and reprobed each time with 26-B. The four phage clones were converted to the pBluescript SK(−) recombinant plasmid by in vivo excision. All four clones contained the same 4.2 kb EcoR1 insert. One clone, designated TpT2-d, was chosen for further analysis. The clone pTpT2-d was not toxic to the *E. coli* cells, and a partial restriction map of the 4.2 kb EcoR1 restriction fragment was generated. Southern blot analysis using the 26-B probe identified a 1.1 kb BamH1-EcoR1 fragment.

EXAMPLE 11

DNA sequences of Tromp1 and Tromp 2

An open reading frame was identified on the 1.1 kb BamH1-EcoR1 fragment encoding 49 amino acids (147 bp). The remainder of the gene was shown to reside on a 3.1 kb EcoR1-BamH1 fragment. All together, the gene was found to consist of an open reading frame of 726 bp. As shown in FIGS. 10 and 11, the sequences of the 867 bp and 919 bp fragments (SEQ ID NO:1 and SEQ ID NO:3, respectively) were obtained using well known dideoxy sequencing techniques of Sanger et al. (See Sambrook, et al., *Molecular Cloning A Laboratory Manual*, Second Edition, Cold Spring Harbor Laboratory Press, 1989). The TROMP1 gene encodes a precursor protein TROMP1 of 288 amino acids (31,742 Da) having the deduced amino acid sequence of SEQ ID NO:2. The TROMP2 gene encodes a precursor protein TROMP2 of 242 amino acids (27,216 Da) having the deduced amino acid sequence of SEQ ID NO:4.

The first 32 residues from the N-terminus of TROMP1 has characteristics of a hydrophobic signal peptide including a 13 residue N-region containing four basic charged residues (Histidine, Lysine, Histidine, and Arginine), an H-region containing 11 consecutive hydrophobic amino acids, and a C-region containing a putative concensus leader peptidase I cleavage site of Threonine-Histidine-Alanine. The first 24 residues from the N-terminus of TROMP2 make up the putative signal peptide containing a carboxy-terminal region with a putative leader peptidase I cleavage site of Leu-Ala-Ala.

The mature processed protein of TROMP 1 consists of 256 amino acids with a calculated mass of 28,182 Da. As determined by inspection and Kyte-Doolittle hydropathy analysis, which identified areas of hydrophobicity and hydrophilicity, the amino acid sequence analysis of the mature protein shows considerable and regular amphiphatic beta-pleated sheet secondary structure corresponding to outer membrane spanning regions. Moreover, the terminal beta-sheet membrane spanning region shows features consistent with other well known gram-negative bacterial outer membrane proteins, including a glycine residue in the terminal 6th position and terminating in phenylalanine.

The mature processed protein of TROMP2 consists of 218 amino acids with a calculated mass of 24,759 Da. The predicted secondary-structure of TROMP2 shows 11 transmembrane segments of amphipatic beta-sheets typical of outer membrane proteins.

The foregoing description of the invention is exemplary for purposes of illustration and explanation. It should be understood that various modifications can be made without departing from the spirit and scope of the invention. Accordingly, the following claims are intended to be interpreted to embrace all such modifications.

SUMMARY OF SEQUENCES

SEQ ID NO:1 is the nucleotide sequence encoding a precursor TROMP-1 protein.

SEQ ID NO:2 is the deduced amino acid sequence of TROMP-1, a precursor TROMP protein encoded by SEQ ID NO:1.

SEQ ID NO:3 is the nucleotide sequence encoding a precursor TROMP-2 protein.

SEQ ID NO:4 is the deduced amino acid sequence of TROMP-2, a precursor TROMP protein encoded by SEQ ID NO:3.

We claim:

1. A nucleic acid that encodes the protein of SEQ ID NO: 4.

2. The nucleic acid of claim 1 comprising the sequence of SEQ ID NO: 3.

3. The nucleic acid of claim 2 wherein T is U.

4. A nucleic acid that is the complement of SEQ ID NO: 3, or a fragment thereof that will selectively hybridize to DNA which encodes the protein of SEQ ID NO: 4.

5. An expression vector comprising the nucleic acid sequence of claim 1.

6. An expression vector comprising the nucleic acid sequence of claim 2.

7. The vector of claim 6, wherein the vector is a plasmid.

8. A host cell stably transformed with the vector of claim 6.

9. The host cell of claim 8, wherein the cell is eukaryotic.

10. The host cell of claim 8, wherein the cell is prokaryotic.

11. A method for preparing an isolated rare outer membrane protein of *T. Pallidum* which comprises culturing the host cell of claim 8, 9 or 10, and recovering a rare outer membrane protein of *T. Pallidum.*

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 957 base pairs
( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: TROMP1

( i x ) FEATURE:
( A ) NAME/KEY: CDS
( B ) LOCATION: 1..954

( x i ) SEQUENCE DESCRIPTION: SEQ ID NO:1:

```
ATG CAT CAA AAT TCA CCC AAG CAG TGT CAC TTG ATA CGT GAA AGA ATA      48
Met His Gln Asn Ser Pro Lys Gln Cys His Leu Ile Arg Glu Arg Ile
  1               5                  10                  15

TGT GCC TGC GTG CTC GCG CTT GGC ATG CTG ACC GGT TTT ACG CAC GCA      96
Cys Ala Cys Val Leu Ala Leu Gly Met Leu Thr Gly Phe Thr His Ala
             20                  25                  30

TTC GGT AGC AAG GAT GCC GCA GCG GAC GGG AAA CCC CTG GTT GTC ACC     144
Phe Gly Ser Lys Asp Ala Ala Ala Asp Gly Lys Pro Leu Val Val Thr
         35                  40                  45

ACC ATT GGC ATG ATA GCG GAT GCT GTC AAA AAC ATC GCT CAA GGT GAT     192
Thr Ile Gly Met Ile Ala Asp Ala Val Lys Asn Ile Ala Gln Gly Asp
     50                  55                  60

GTG CAT CTA AAG GGG TTG ATG GGT CCT GGT GTT GAC CCG CAC CTG TAC     240
Val His Leu Lys Gly Leu Met Gly Pro Gly Val Asp Pro His Leu Tyr
 65                  70                  75                  80

ACG GCT ACT GCG GGG GAT GTG GAA TGG CTC GGG AAT GCG GAT CTC ATC     288
Thr Ala Thr Ala Gly Asp Val Glu Trp Leu Gly Asn Ala Asp Leu Ile
                 85                  90                  95
```

-continued

CTG TAC AAC GGG TTG CAC CTG GAA ACC AAG ATG GGC GAG GTG TTT TCC 336
Leu Tyr Asn Gly Leu His Leu Glu Thr Lys Met Gly Glu Val Phe Ser
100 105 110

AAA CTG CGC GGG AGC CGC TTG GTA GTT GCA GTT TCT GAG ACT ATT CCG 384
Lys Leu Arg Gly Ser Arg Leu Val Val Ala Val Ser Glu Thr Ile Pro
115 120 125

GTG TCT CAG CGT CTT TCT CTT GAG GAA GCA GAG TTC GAT CCG CAT GTG 432
Val Ser Gln Arg Leu Ser Leu Glu Glu Ala Glu Phe Asp Pro His Val
130 135 140

TGG TTT GAT GTA AAG CTG TGG TCT TAT TCG GTG AAG GCA GTG TAC GAA 480
Trp Phe Asp Val Lys Leu Trp Ser Tyr Ser Val Lys Ala Val Tyr Glu
145 150 155 160

AGC TTG TGC AAG CTG TTG CCG GGA AAA ACT CGC GAA TTT ACT CAA CGT 528
Ser Leu Cys Lys Leu Leu Pro Gly Lys Thr Arg Glu Phe Thr Gln Arg
165 170 175

TAT CAG GCG TAC CAG CAG CAG TTG GAT AAG CTT GAC GCG TAC GTT CGG 576
Tyr Gln Ala Tyr Gln Gln Gln Leu Asp Lys Leu Asp Ala Tyr Val Arg
180 185 190

CGC AAG GCG CAG TCG CTG CCT GCT GAA AGG CGT GTG TTG GTG ACC GCT 624
Arg Lys Ala Gln Ser Leu Pro Ala Glu Arg Arg Val Leu Val Thr Ala
195 200 205

CAT GAT GCG TTC GGC TAT TTT AGC CGT GCG TAT GGT TTT GAG GTG AAG 672
His Asp Ala Phe Gly Tyr Phe Ser Arg Ala Tyr Gly Phe Glu Val Lys
210 215 220

GGG TTG CAA GGG GTG AGC ACC GCT TCG GAA GCC AGT GCG CAT GAT ATG 720
Gly Leu Gln Gly Val Ser Thr Ala Ser Glu Ala Ser Ala His Asp Met
225 230 235 240

CAG GAA CTG GCA GCG TTT ATT GCG CAG CGT AAA CTC CCT GCT ATC TTT 768
Gln Glu Leu Ala Ala Phe Ile Ala Gln Arg Lys Leu Pro Ala Ile Phe
245 250 255

ATT GAG AGT TCT ATT CCG CAC AAA AAC GTT GAA GCG TTA AGG GAT GCG 816
Ile Glu Ser Ser Ile Pro His Lys Asn Val Glu Ala Leu Arg Asp Ala
260 265 270

GTG CAG GCA AGA GGG CAC GTA GTG CAG ATT GGA GGC GAG TTG TTT TCT 864
Val Gln Ala Arg Gly His Val Val Gln Ile Gly Gly Glu Leu Phe Ser
275 280 285

GAT GCG ATG GGG GAT GCG GGT ACG AGC GAG GGT ACC TAC GTA GGG ATG 912
Asp Ala Met Gly Asp Ala Gly Thr Ser Glu Gly Thr Tyr Val Gly Met
290 295 300

GTA ACA CAC AAT ATC GAT ACG ATC GTT GCT GCG TTG GCT CGC 954
Val Thr His Asn Ile Asp Thr Ile Val Ala Ala Leu Ala Arg
305 310 315

TAG 957

( 2 ) INFORMATION FOR SEQ ID NO:2:

( i ) SEQUENCE CHARACTERISTICS:
( A ) LENGTH: 318 amino acids
( B ) TYPE: amino acid
( D ) TOPOLOGY: linear ( i i ) MOLECULE TYPE: protein ( x i ) SEQUENCE DESCRIPTION: SEQ ID NO:2:

Met His Gln Asn Ser Pro Lys Gln Cys His Leu Ile Arg Glu Arg Ile
1 5 10 15

Cys Ala Cys Val Leu Ala Leu Gly Met Leu Thr Gly Phe Thr His Ala
20 25 30

Phe Gly Ser Lys Asp Ala Ala Ala Asp Gly Lys Pro Leu Val Val Thr
35 40 45

Thr Ile Gly Met Ile Ala Asp Ala Val Lys Asn Ile Ala Gln Gly Asp

-continued 50 55 60

Val His Leu Lys Gly Leu Met Gly Pro Gly Val Asp Pro His Leu Tyr
65 70 75 80

Thr Ala Thr Ala Gly Asp Val Glu Trp Leu Gly Asn Ala Asp Leu Ile
85 90 95

Leu Tyr Asn Gly Leu His Leu Glu Thr Lys Met Gly Glu Val Phe Ser
100 105 110

Lys Leu Arg Gly Ser Arg Leu Val Val Ala Val Ser Glu Thr Ile Pro
115 120 125

Val Ser Gln Arg Leu Ser Leu Glu Glu Ala Glu Phe Asp Pro His Val
130 135 140

Trp Phe Asp Val Lys Leu Trp Ser Tyr Ser Val Lys Ala Val Tyr Glu
145 150 155 160

Ser Leu Cys Lys Leu Leu Pro Gly Lys Thr Arg Glu Phe Thr Gln Arg
165 170 175

Tyr Gln Ala Tyr Gln Gln Gln Leu Asp Lys Leu Asp Ala Tyr Val Arg
180 185 190

Arg Lys Ala Gln Ser Leu Pro Ala Glu Arg Arg Val Leu Val Thr Ala
195 200 205

His Asp Ala Phe Gly Tyr Phe Ser Arg Ala Tyr Gly Phe Glu Val Lys
210 215 220

Gly Leu Gln Gly Val Ser Thr Ala Ser Glu Ala Ser Ala His Asp Met
225 230 235 240

Gln Glu Leu Ala Ala Phe Ile Ala Gln Arg Lys Leu Pro Ala Ile Phe
245 250 255

Ile Glu Ser Ser Ile Pro His Lys Asn Val Glu Ala Leu Arg Asp Ala
260 265 270

Val Gln Ala Arg Gly His Val Val Gln Ile Gly Gly Glu Leu Phe Ser
275 280 285

Asp Ala Met Gly Asp Ala Gly Thr Ser Glu Gly Thr Tyr Val Gly Met
290 295 300

Val Thr His Asn Ile Asp Thr Ile Val Ala Ala Leu Ala Arg
305 310 315

( 2 ) INFORMATION FOR SEQ ID NO:3:

( i ) SEQUENCE CHARACTERISTICS:
( A ) LENGTH: 729 base pairs
( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: TROMP2

( i x ) FEATURE:
( A ) NAME/KEY: CDS
( B ) LOCATION: 1..726

( x i ) SEQUENCE DESCRIPTION: SEQ ID NO:3:

ATG AAA CAG GGC TGT TTT ATG GTG GCG GGC TTT GCG CTG ACG TGC GCG 48
Met Lys Gln Gly Cys Phe Met Val Ala Gly Phe Ala Leu Thr Cys Ala
1 5 10 15

TTT TTG GTG TCC CCC CTT GCG GCG CAA AGG TCG AAG GTC AAT TAC CAG 96
Phe Leu Val Ser Pro Leu Ala Ala Gln Arg Ser Lys Val Asn Tyr Gln
20 25 30

GCA TAC TTC ATA GAT GAC TTT GAC GGT GCC TCC GAG GAT CAG GGT CTC 144
Ala Tyr Phe Ile Asp Asp Phe Asp Gly Ala Ser Glu Asp Gln Gly Leu

-continued

```
                35                            40                            45

GCC TGG CGT GCT GCG GGG AGC AAG TTC ATC ACA AAG GGC TTC CCT ATC      192
Ala Trp Arg Ala Ala Gly Ser Lys Phe Ile Thr Lys Gly Phe Pro Ile
     50                      55                      60

CTC AAG TAT TTC GAG GGC ATG CCA CAG GCG GTG CGC ATG GCG GGC TCG      240
Leu Lys Tyr Phe Glu Gly Met Pro Gln Ala Val Arg Met Ala Gly Ser
 65                      70                      75                      80

TGG CAA GGG AAG GAC AAG GAA GCC CGG TTC ATC GGA GTA GAG TGC AAG      288
Trp Gln Gly Lys Asp Lys Glu Ala Arg Phe Ile Gly Val Glu Cys Lys
                 85                      90                      95

TTC AAT CGA CAG GGG AAT AAC TGG CTG GAC CTA ATT CCG ACT AAG GGT      336
Phe Asn Arg Gln Gly Asn Asn Trp Leu Asp Leu Ile Pro Thr Lys Gly
            100                     105                     110

GGT AGC GAT TAC GAG ATC CCC CTG CGT GGG GTG GTC AGT GGG TTC GAC      384
Gly Ser Asp Tyr Glu Ile Pro Leu Arg Gly Val Val Ser Gly Phe Asp
        115                     120                     125

GTG TGG GTG TGG GGT GCA GGT TAT CAG TAC TCG CTC GAG GCT TTG GTT      432
Val Trp Val Trp Gly Ala Gly Tyr Gln Tyr Ser Leu Glu Ala Leu Val
    130                     135                     140

AGG GAC TGC ACG GGA CGA GTC CAC ACC CTC CTA ATA GGC AAC CTC GAC      480
Arg Asp Cys Thr Gly Arg Val His Thr Leu Leu Ile Gly Asn Leu Asp
145                     150                     155                     160

TTC CAA GGG TGG AAG AAC CTT AGT GTT TCG GTT CCC ACA CAC ATC CCA      528
Phe Gln Gly Trp Lys Asn Leu Ser Val Ser Val Pro Thr His Ile Pro
                165                     170                     175

CAG ACG TCG CGC TAT TTG GGG AGC GCG CAA CAC CTG AGT TTT GTC GGT      576
Gln Thr Ser Arg Tyr Leu Gly Ser Ala Gln His Leu Ser Phe Val Gly
            180                     185                     190

TTC AGG ATC CGT ACT AGC CCA TCA GAG CGG GTG GAT GAT TTC TAC GTG      624
Phe Arg Ile Arg Thr Ser Pro Ser Glu Arg Val Asp Asp Phe Tyr Val
        195                     200                     205

TTC TTT GAC CAG TTC AAG GCG CTT GCT AAC ATG CAT ATC GAC TTT TAC      672
Phe Phe Asp Gln Phe Lys Ala Leu Ala Asn Met His Ile Asp Phe Tyr
    210                     215                     220

GAT GGA CAC GAG TTG AGA AAT GCT CAG TTC AAG GAG GAA GGA GAG AGC      720
Asp Gly His Glu Leu Arg Asn Ala Gln Phe Lys Glu Glu Gly Glu Ser
225                     230                     235                     240

GGC AAA TGA                                                          729
Gly Lys
```

( 2 ) INFORMATION FOR SEQ ID NO:4:

( i ) SEQUENCE CHARACTERISTICS:
( A ) LENGTH: 242 amino acids
( B ) TYPE: amino acid
( D ) TOPOLOGY: linear ( i i ) MOLECULE TYPE: protein ( x i ) SEQUENCE DESCRIPTION: SEQ ID NO:4:

```
Met Lys Gln Gly Cys Phe Met Val Ala Gly Phe Ala Leu Thr Cys Ala
  1               5                  10                  15

Phe Leu Val Ser Pro Leu Ala Ala Gln Arg Ser Lys Val Asn Tyr Gln
             20                  25                  30

Ala Tyr Phe Ile Asp Asp Phe Asp Gly Ala Ser Glu Asp Gln Gly Leu
         35                  40                  45

Ala Trp Arg Ala Ala Gly Ser Lys Phe Ile Thr Lys Gly Phe Pro Ile
     50                  55                  60

Leu Lys Tyr Phe Glu Gly Met Pro Gln Ala Val Arg Met Ala Gly Ser
 65                  70                  75                  80
```

-continued

| | | | | | | | | | | | | | | | |
|---|---|---|---|---|---|---|---|---|---|---|---|---|---|---|---|
| Trp | Gln | Gly | Lys | Asp<br>85 | Lys | Glu | Ala | Arg | Phe<br>90 | Ile | Gly | Val | Glu | Cys<br>95 | Lys |
| Phe | Asn | Arg | Gln<br>100 | Gly | Asn | Asn | Trp | Leu<br>105 | Asp | Leu | Ile | Pro | Thr<br>110 | Lys | Gly |
| Gly | Ser | Asp<br>115 | Tyr | Glu | Ile | Pro | Leu<br>120 | Arg | Gly | Val | Val | Ser<br>125 | Gly | Phe | Asp |
| Val | Trp<br>130 | Val | Trp | Gly | Ala | Gly<br>135 | Tyr | Gln | Tyr | Ser | Leu<br>140 | Glu | Ala | Leu | Val |
| Arg<br>145 | Asp | Cys | Thr | Gly | Arg<br>150 | Val | His | Thr | Leu | Leu<br>155 | Ile | Gly | Asn | Leu | Asp<br>160 |
| Phe | Gln | Gly | Trp | Lys<br>165 | Asn | Leu | Ser | Val | Ser<br>170 | Val | Pro | Thr | His | Ile<br>175 | Pro |
| Gln | Thr | Ser | Arg<br>180 | Tyr | Leu | Gly | Ser | Ala<br>185 | Gln | His | Leu | Ser | Phe<br>190 | Val | Gly |
| Phe | Arg | Ile<br>195 | Arg | Thr | Ser | Pro | Ser<br>200 | Glu | Arg | Val | Asp | Asp<br>205 | Phe | Tyr | Val |
| Phe | Phe<br>210 | Asp | Gln | Phe | Lys | Ala<br>215 | Leu | Ala | Asn | Met | His<br>220 | Ile | Asp | Phe | Tyr |
| Asp<br>225 | Gly | His | Glu | Leu | Arg<br>230 | Asn | Ala | Gln | Phe | Lys<br>235 | Glu | Glu | Gly | Glu | Ser<br>240 |
| Gly | Lys | | | | | | | | | | | | | | |